United States Patent [19]
Adams et al.

[11] Patent Number: 5,140,047
[45] Date of Patent: Aug. 18, 1992

[54] LIPOXYGENASE INHIBITORS

[75] Inventors: Jerry L. Adams; Ravi S. Garigipati, both of Wayne, Pa.

[73] Assignee: SmithKline Beecham Corporation, Philadelphia, Pa.

[21] Appl. No.: 695,115

[22] Filed: May 3, 1991

[51] Int. Cl.$^5$ .................... A61K 31/17; C07D 275/64
[52] U.S. Cl. .................... 514/575; 514/307; 514/311; 514/357; 514/553; 546/149; 546/176; 546/337; 548/189; 548/235; 548/247; 549/77; 549/496; 562/621; 562/623; 562/874
[58] Field of Search .................... 546/149, 176, 337; 548/189, 235, 247; 562/621, 623, 874; 549/71, 496; 514/575, 307, 311, 357, 553

[56] References Cited

U.S. PATENT DOCUMENTS

| | | | |
|---|---|---|---|
| 4,005,140 | 1/1977 | Spicer et al. | 260/553 |
| 4,605,669 | 8/1986 | Summers | 514/575 |
| 4,738,986 | 4/1988 | Kneen et al. | 514/575 |
| 4,769,461 | 9/1988 | Musser et al. | 546/152 |
| 4,906,666 | 3/1990 | Reinholz et al. | 514/575 |
| 4,906,667 | 3/1990 | Varma et al. | 514/575 |
| 4,981,865 | 1/1991 | Belliotti et al. | 514/480 |
| 5,006,534 | 4/1991 | Mohrs et al. | 514/311 |
| 5,036,157 | 7/1991 | Kneen et al. | 562/623 |

FOREIGN PATENT DOCUMENTS 0196184 10/1986 European Pat. Off. .
0196674 10/1986 European Pat. Off. .
378991A 7/1990 European Pat. Off. .
0384594 8/1990 European Pat. Off. .

OTHER PUBLICATIONS

Bhattacherjee et al., *Anal. N.Y. Acad of Sciences*, vol. 524, pp. 307–320 (1988).
Summers et al., *J. Med. Chem.*, vol. 30, pp. 574–580 (1987).
Summers et al., *J. Med. Chem.*, vol. 30, pp. 2121–2126 (1987).
Summers et al., *J. Med. Chem.*, vol. 31, pp. 3–5 (1988).
Summers et al., *J. Med Chem.*, vol. 31, pp. 1960–1964 (1988).
Jackson et al., *J. Med Chem.*, vol. 31, pp. 500–503 (1988).
Summers et al., *J Med Chem.*, vol. 33, pp. 992–998 (1988).
Derwent Abstract 91-046051/07 [EP412939-A] published Feb. 13, 1991.

*Primary Examiner*—Bernard Dentz
*Attorney, Agent, or Firm*—Dara L. Dinner; Stephen Venetianer; Edward T. Lentz

[57] ABSTRACT

Tricyclic hydroxyurea and hydroxamate compounds, pharmaceutical compositions, and their use as as inhibitors of the oxidation of polyunsaturated fatty acids, such as by inhibition on the 5-lipoxygenase enzyme, and treatment of diseases therein.

20 Claims, No Drawings

LIPOXYGENASE INHIBITORS

FIELD OF THE INVENTION

This invention relates to novel compounds, pharmaceutical compositions and methods for inhibiting oxygenated polyunsaturated fatty acid metabolism and disease states caused thereby. Specifically inhibited is the lipoxygenase enzyme pathway of arachidonic acid metabolism in an animal.

BACKGROUND OF THE INVENTION

The metabolism of arachidonic acid occurs by many pathways. One route of metabolism is via the cyclooxygenase (CO) mediated pathway which produces $PGH_2$ which is in turn metabolized to the prostanoids ($PGE_2$, $TxA_2$, and prostacyclin). These products are produced by various cells including polymorphonuclear leukocytes, mast cells and monocytes. Another route is by the lipoxygenase mediated pathway which oxidizes arachidonic acid initially to 5-hydroperoxy-eicosatetraenoic acid (5-HPETE) which is further metabolized to $LTA_4$, the precursor to the peptidoleukotrienes ($LTC_4$, $LTD_4$, and $LTE_4$) and $LTB_4$. Additionally 5-HPETE is converted to 5-hydroxyeicosatetraenoic acid (5-HETE).

Lipoxygenases are classified according to the position in the arachidonic acid which is oxygenated. Platelets metabolize arachidonic acid to 12-HETE, while polymorphonuclear leukocytes (PMNs) contain 5 and 15 lipoxygenases. It is known that 12-HETE and 5,12-diHETE are chemotactic for human neutrophils and eosinophils, and may augment the inflammation process. 5-HPETE is known to be a precursor to the peptidylleukotrienes, formerly known as slow reacting substance of anaphylaxis (SRS-A) and $LTB_4$. The SRS family of molecules, such as leukotrienes $C_4$ and $D_4$ have been shown to be potent bronchoconstrictors. $LTB_4$ has been shown to be a potent chemotatic for PMNs. The products of the 5-lipoxygenase pathway are believed to play an important role in initiating and maintaining the inflammatory response of asthma, allergy, arthritis, psoriasis, and inflammatory bowel disease. It is believed that blockage of this enzyme will interrupt the various pathways involved in these disease states and as such inhibitors should be useful in treating a variety of inflammatory diseases, such as those enumerated above. The absence of selective inhibitors of lipoxygenase, as opposed to cyclooxygenase, which are active in vivo has prevented adequate investigation of the role of leukotrienes in inflammation.

The arachidonic acid oxygenated products, as noted above, have been identified as mediators of various inflammatory conditions. The various inflammatory disease states caused by these mediators and many other conditions, as discussed herein, are all conditions in which an oxygenated polyunsaturated fatty acid metabolite inhibitor, such as a 5-LO inhibitor, would be indicated.

There remains a need for treatment, in this field, for compounds which are capable of inhibiting the oxygenation of arachidonic acid by inhibition of enzymes such as lipoxygenase, specifically 5-lipoxygenase (5-LO) thereby preventing the formation of various leukotrienes and prostaglandins.

SUMMARY OF THE INVENTION

This invention relates to a compound of the formula (I)

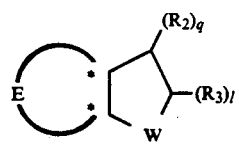

Formula (I)

wherein
$R_2$ and $R_3$ are

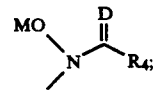

D is oxygen or sulfur;

M is hydrogen, a pharmaceutically acceptable cation, aroyl or $C_{1-12}$ alkoyl;

$R_4$ is $NR_5R_6$; $alkyl_{1-6}$; alkyl substituted by halogen or hydroxyl; $alkenyl_{2-6}$; aryl or heteroaryl optionally substituted by halogen, $alkyl_{1-6}$, halosubstituted $alkyl_{1-6}$, hydroxyl, or $alkoxy_{1-6}$;

$R_5$ is H or $alkyl_{1-6}$;

$R_6$ is H; $alkyl_{1-6}$; aryl; heteroaryl; arylalkyl; alkyl substituted by halogen or hydroxyl; aryl, heteroaryl, arylalkyl, or heteroarylalkyl substituted by halo, cyano, $alkyl_{1-12}$, $alkoxy_{1-6}$, halosubstituted $alkyl_{1-6}$, alkylthio, alkylsulphonyl, or alkylsulfinyl; or $R_5$ and $R_6$ may together form a ring having 5 to 7 members, which may optionally contain a heteroatom selected from oxygen, sulfur or nitrogen;

W is $CH_2(CH_2)_s$, $O(CH_2)_s$, $S(CH_2)_s$, or $NR_7(CH_2)_s$;

$R_7$ is hydrogen, $C_{1-4}$ alkyl, aryl, aryl $C_{1-6}$ alkyl, $C_{1-6}$ alkoyl, or aroyl;

s is a number having a value of 0 to 2; provided that when 1 is one and W is $O(CH_2)_s$, or $S(CH_2)_s$, then s is 1 to 2; and when W is $NR_7(CH_2)_s$ then s is 1 to 2 and q is 1;

q is a number having a value of 0 or 1;

l is a number having a value of 0 or 1; provided that when q is 0 then is 1, and $R_2$ is hydrogen and when q is 1 is 0 and $R_3$ is hydrogen;

E is selected from

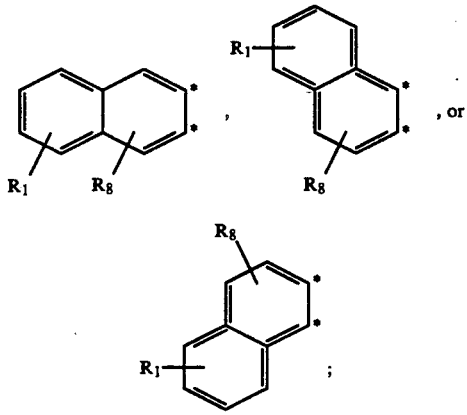

the asterix * denoting point of attachment of the ring;

$R_1$ and $R_8$ are independently selected from the group consisting of hydrogen, halo, alkyl$_{1-10}$, halo-substituted $C_{1-10}$ alkyl, hydroxy-substituted $C_{1-10}$ alkyl, alkoxy$_{1-10}$, —(CH$_2$)$_p$CO$_2$R$_5$, (CH$_2$)$_m$—Ar—(X)$_v$, O(CH$_2$)$_m$Ar—(X)$_v$, or S(CH$_2$)$_m$—Ar—(X)$_v$, provided that at least one of $R_1$ or $R_8$ is hydrogen, $C_{1-10}$ alkoxy, or halo;

m is a number having a value of 0 to 3;

p is a number having a value of 0 to 10;

v is a number having a value of 1 to 3;

Ar is a member selected from the group consisting of phenyl, naphthyl, quinolyl, isoquinolyl, pyridyl, furanyl, imidazoyl, benzimidazoyl, triazolyl, oxazolyl, isoxazolyl, thiazole, or thienyl;

X is a member selected from the group consisting of hydrogen, halogen, alkyl$_{1-5}$, cycloalkyl$_{5-8}$, hydroxy, (CHY)$_t$carboxy, O-alkyl$_{1-5}$, S(O)$_n$-alkyl$_{1-5}$, halosubstituted alkyl$_{1-5}$, (CHY)$_t$N(R$_5$)$_2$ or cyano; provided that if v is a number greater than 1 then one substituent must be selected from alkyl, O-alkyl$_{1-5}$, or halo;

Y is hydrogen or alkyl$_{1-3}$;

n is a number having a value of 0 to 2;

t is a number having a value of 0 or 1;

and the pharmaceutically acceptable salts thereof useful as inhibitors of oxygenated polyunsaturated fatty acids (hereinafter OPUFA).

This invention also relates to a pharmaceutical composition comprising a pharmaceutically acceptable carrier or diluent and an effective amount of an OPFUA pathway inhibiting compound of Formula (I) as defined above, or a pharmaceutically acceptable salt thereof.

This invention also relates to a method of treating an OPUFA mediated disease in an animal in need thereof which comprises administering to such animal, including humans, an effective amount of a compound of Formula (I) or pharmaceutically acceptable salts thereof.

More specifically this invention relates to a method of treating a lipoxygenase pathway mediated disease in an animal, including humans, in need thereof which comprises administering to such animal an effective, nontoxic lipoxygenase pathway inhibiting amount of a compound of Formula (I) or a pharmaceutically acceptable salt thereof.

This invention also relates to a method of treating an OPUFA mediated disease in an animal in need thereof which comprises administering to such animal, including humans, an effective amount of a compound of Formula (II) or pharmaceutically acceptable salts thereof.

DETAILED DESCRIPTION OF THE INVENTION

This invention relates to compounds of Formula (I) as described above, pharmaceutical compositions comprising a pharmaceutically acceptable carrier or diluent and a compound of Formula (I) and pharmaceutically acceptable salts thereof, methods of treating an OPUFA mediated disease, specifically a 5-lipoxygenase pathway mediated disease comprising administration of a compound of Formula (I) and salts thereof.

This invention also relates to compounds of Formula (II) as described herein, pharmaceutical compositions comprising a pharmaceutically acceptable carrier or diluent and a compound of Formula (II) and pharmaceutically acceptable salts thereof, methods of treating an OPUFA mediated disease, specifically a 5-lipoxygenase pathway mediated disease comprising administration of a compound of Formula (II) and pharmaceutically acceptable salts thereof.

The compounds of Formula (I) have been found to be useful in inhibiting the enzymes involved in the oxygenated polyunsaturated fatty acid pathway which includes the metabolism of arachidonic acid, in an animal in need thereof.

A preferred embodiment of the present invention is where q is 1 and l is 0. Another preferred embodiment is when $R_8$ is hydrogen or halo; $R_1$ is selected from hydrogen, halogen, halosubstituted alkyl, alkoxy, (CH$_2$)$_p$CO$_2$R$_5$, O(CH$_2$)$_m$—Ar—(X)$_v$, or (CH$_2$)$_m$—Ar—(X)$_v$; p is a number having a value of 0 to 8, m is a number having a value of 0 to 2; v is a number having a value of 1 to 2; W is CH$_2$(CH$_2$)$_s$ or O(CH$_2$)$_s$, s is a number having a value of 0 or 1. Preferred X groups are hydrogen, methoxy, halo, and CF$_3$. When X is (CHY)$_t$N(R$_5$)$_2$ the $R_5$ group is independently selected from hydrogen or an alkyl of 1-6 carbons yielding an unsubstituted, mono- or di-substituted amine component.

More preferred are the compounds wherein $R_1$ is hydrogen, halogen, methoxy, ethoxy, propyloxy, or phenoxy. Most preferred is where W is CH$_2$(CH$_2$)$_s$ and s is 0 or 1, or O(CH$_2$)$_s$, and s is 0; $R_1$ is hydrogen, halogen, or $C_{1-3}$ alkoxy, and the E ring is an anthracene like derivative relative to the W containing ring.

A further preferred embodiment of the present invention is where D is oxygen. More preferred is where $R_4$ is NR$_5$R$_6$ or alkyl$_{1-6}$; q is 1 and l is 0. Preferred ring placement for the $R_1$ and $R_8$ moieties for the formula (I) compounds is shown below, for illustrative purposes only, using the numbered structures (A) and (B). When W is CH$_2$(CH$_2$)$_s$ and s is 1, see structure (A), preferred substitution is on the 5-, 6-, 7-, or 10-position(s); and when s is 0 the preferred substitution is on the 4-, 5-, 6- and 9-position(s); applicable substitution patterns are also preferred when W is O(CH$_2$)$_s$. For those compounds whose ring system corresponds to (B), as shown below, when W is CH$_2$(CH$_2$)$_s$ and s is 1, ring position 5-, 6-, 7- and 8- are preferred. Similar preferred patterns for s is 0 follow as well, i.e., the 4-, 5- 6- and 7-positions.

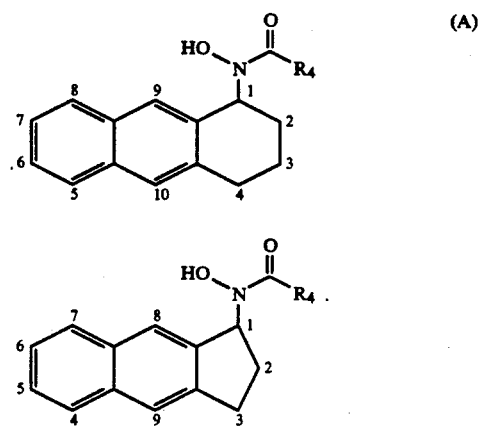

(B)

[Structure B: tetrahydrophenanthrene-like ring system with HO—N(—R4)—C(=O) substituent, positions numbered 1-10]

The terms "aryl" or "heteroaryl" are used herein at all occurrences to mean substituted and unsubstituted aromatic ring(s) or ring systems containing from 5 to 10 carbon atoms, which may include bi- or tri-cyclic systems and may include, but are not limited to heteroatoms selected from O, N, or S. Representative examples include, but are not limited to, phenyl, naphthyl, pyridyl, quinolinyl, thiazinyl, and furanyl.

The terms "lower alkyl" or "alkyl" are used herein at all occurrences to mean straight or branched chain radical of 1 to 10 carbon atoms, unless the chain length is limited thereto, including, but not limited to methyl, ethyl, n-propyl, isopropyl, n-butyl, sec-butyl, isobutyl, tert-butyl, and the like.

The term "alkenyl" is used herein at all occurrences to mean straight or branched chain radical of 2-10 carbon atoms, unless the chain length is limited thereto, including, but not limited to ethenyl, 1-propenyl, 2-propenyl, 2-methyl-1-propenyl, 1-butenyl, 2-butenyl and the like.

The term "aralkyl" or "heteroarylalkyl" is used herein to mean $C_{1-4}$ Ar, wherein Ar is as defined above.

The term "aroyl" is used herein to mean —C(O) Ar, wherein Ar is as defined above and in Formula (I), including, but not limited to benzoyl, 1- or 2-naphthoyl and the like.

The term "alkoyl" is used herein to mean —C(O)C$_{1-10}$alkyl wherein alkyl is as defined above, including, but not limited to methyl, ethyl, isopropyl, n-butyl, t-butyl, and the like.

The term "cycloalkyl" is used herein to mean cyclic radicals, preferably of 3 to 8 carbons, including but not limited to cyclopropyl, cyclopentyl, cyclohexyl, and the like.

The term "halo" or "halogen" are used interchangeably herein to mean radicals derived from the elements fluorine, chlorine, bromine, and iodine.

The term "lipoxygenase" is used herein to mean the 5-, 12-, or 15-lipoxygenase enzymes.

By the term "OPUFA mediated disease or disease state" is meant any disease state which is mediated (or modulated) by oxidized polyunsaturated fatty acids, specifically the arachidonic acid metabolic pathway. The oxidation of arachidonic acid by such enzymes as the lipoxygenase enzymes is specifically targeted by the present invention. Such enzymes include, but are not limited to, 5-LO, 12-LO, and 15-LO; which produce the following mediators, including but not limited to, LTB$_4$, LTC$_4$, LTD$_4$, 5,12-diHETE, 5-HPETE, 12-HPETE, 15-HPETE, 5-HETE, 12-HETE and 15-HETE.

By the term "OPUFA interfering amount" is meant an effective amount of a compound of Formula (I) or (II) which shows a reduction of the in vivo levels of an oxygenated polyunsaturated fatty acid, preferably an arachidonic acid metabolite.

The compounds of the present invention may contain one or more asymmetric carbon atoms and may exist in racemic and optically active forms. All of these compounds are contemplated to be within the scope of the present invention.

Some preferred compounds which are themselves within the scope of the present invention include the following:

N-1-(1,2,3,4-Tetrahydrophenanthrenyl)-N-hydroxyurea;
N-1-(1,2,3,4-Tetrahydrocyclohepta[a]naphthalenyl)-N-hydroxyurea;
N-1-(1,2-Dihydro-cyclopenta[a]naphthalenyl)-N-hydroxyurea;
N-{1-(1,2-Dihydronaphtho[2,1-b]furyl}-N-hydroxyurea
N-{3-(2,3-Dihydronaphtho[1,2-b]furyl}-N-hydroxyurea
N-1-(Naphtho[2,3-b]thiophenyl)-N-hydroxyurea; or
N-1-(Chloronaphtho[1,2-b]furanyl)-N-hydroxyurea.

Useful intermediates of the present invention are the novel hydroxylamine derivatives of Formula (II);

FORMULA (II)

[Structure: bicyclic ring system with E ring fused to W-containing ring, bearing (R'$_2$)$_q$ and (R'$_3$)$_l$ substituents]

wherein R'$_2$ and R'$_3$ are $$-\underset{A}{\underset{|}{N}}-OB$$

B$_1$ is hydrogen, benzyl, optionally substituted benzyl, Si(R$_x$)$_3$, C(O)R'$_5$, C(O)OR'$_5$, CH$_2$OCH$_2$CH$_2$Si(R$_x$)$_3$, C$_1$alkyl-C$_{1-3}$alkoxy, C$_1$alkylC$_2$alkoxyC$_{1-3}$alkoxy, or tetrahydropyranyl;

A is hydrogen or C(O)OR$_z$;

R$_z$ is benzyl, Si(R$_x$)$_3$, t-butyl, or CH$_2$OCH$_2$CH$_2$Si(R$_x$)$_3$;

R'$_5$ is C$_{1-6}$ alkyl, aryl, or aralkyl;

R$_x$ is independently selected from alkyl or aryl; and all the remaining variables, such as E, R$_8$, R$_1$, W, Ar, X, Y, R$_7$, m, n, s, t, q, l, and v are as defined for Formula (I).

Preferred B$_1$ substituent groups are tetrahydropyranyl; CH$_2$OCH$_3$ when B$_1$ is C$_1$alkylC$_{1-3}$alkoxy; CH$_2$OCH$_2$CH$_2$OCH$_3$ when B$_1$ is C$_1$alkylC$_2$alkoxyC$_{1-3}$alkoxy; C(O)R'$_5$ and C(O)OR'$_5$ with R'$_5$ as a C$_{1-6}$ alkyl, specifically methyl, t-butyl, or phenyl group and benzyl when R'$_5$ is an aralkyl group. When R'$_2$ or B$_1$ is CH$_2$OCH$_2$CH$_2$Si(R$_x$)$_3$, the R$_x$ moiety is preferably CH$_3$. When B$_1$ is an optionally substituted benzyl the substituent groups are selected from C$_{1-6}$ alkoxy or C$_{1-6}$ alkyl.

The hydroxylamine derivatives of Formula II are easily converted to the compounds of Formula (I) wherein R$_4$ is NHR$_5$R$_6$ or a hydroxamate derivative using art known procedures. Various illustrative methods to prepare compounds of Formula (I) are given in for various other hydroxyurea/hydroxamate compounds in Summers et al., U.S. Pat. No. 4,873,259, issued Oct. 10, 1989, pages 7-11 whose disclosure is incorporated by reference herein.

Preferred hydroxylamines of the instant invention are:

N-{1-(1,2-Dihydronaphtho[2,1-b]furyl}-N-hydroxyamine;

N-{3-(2,3-Dihydronaphtho[1,2-b]furyl}-N-hydroxyamine; or

N-1-(1,2,3,4-Tetrahydrophenanthrenyl)-N-hydroxyamine.

As a general summary of the synthetic pathways described in greater detail below the compounds of Formula (I) and (II) can be produced by the following means:

The compounds of Formula (I) can be produced by a process which comprises

A. reacting a compound of Formula (II) as described above, wherein $B_1$ is hydrogen, (i) with trimethylsilyl isocyanate (TMSNCO), followed by work up with ammonium chloride to yield a hydroxyurea derivative of a Formula (I) compound wherein $R_4$ is $NH_2$; or (ii) with sodium or potassium cyanate in an acidic solution to yield a hydroxyurea derivative of a Formula (I) compound wherein $R_4$ is $NH_2$; or (iii) with gaseous HCl, followed by treatment with phosgene or a phosgene equivalent, resulting in the corresponding carbamoyl chloride intermediate; or an alkylchloroformate, such as ethyl chloroformate, resulting in the corresponding carbamate; which is reacted with aqueous ammonia, or a substituted amine to yield an optionally substituted hydroxyurea derivative of a Formula (I) compound; or (iv) with acetyl chloride and organic solvent, such as triethylamine, to yield the N,O-diacetate derivative followed by hydrolysis with an alkali hydroxide, such as lithium hydroxide, to yield a compound of Formula (I) wherein $R_4$ is other than $NR_5R_6$; or (v) with an acylating agent, such as acetic anhydride in the presence of a base, such as pyridine, followed by hydrolysis with an alkali hydroxide, such as lithium hydroxide, to yield a compound of Formula (I) wherein $R_4$ is a hydroxamic acid derivative; or B. reacting a compound of Formula (II) as described above, wherein $B_1$ is a benzyl, substituted benzyl or a benzyl carbonate protecting group, with (i) acetyl chloride in an organic solvent to yield a protected hydroxamic acid derivative of Formula (I) compounds, which is then deprotected, optionally by hydrogenation or with ethane thiol in the presence of aluminium trichloride, to yield a compound of Formula (I) wherein $R_4$ is other than $NR_5R_6$; or (ii) trimethylsilyl isocyanate as in step A above, to yield protected hydroxyurea derivatives of Formula (I) compounds which is then deprotected, optionally by hydrogenation or with ethane thiol in the presence of aluminium trichloride, to yield a compound of Formula (I); or (iii) phosgene or a phosgene equivalent, resulting in the corresponding carbamoyl chloride intermediate; or an alkylchloroformate, such as ethyl chloroformate, resulting in the corresponding carbamate, which is reacted with aqueous ammonia, or a substituted amine; which is then deprotected, optionally by hydrogenation or with ethane thiol in the presence of aluminium trichloride, to yield a compound of Formula (I); or (iv) sodium or potassium cyanate in an acidic solution which is then deprotected, optionally by hydrogenation or with ethane thiol in the presence of aluminium trichloride, to yield a compound of Formula (I); or C. reacting a compound of Formula (II) as described above, wherein $B_1$ is $Si(R_x)_3$, or $CH_2OCH_2CH_2Si(R_x)_3$ with (i) sodium or potassium cyanate in an acidic solution and deprotected by use of anhydrous fluoride $(R_4N^+)F^-$, or under mildly acidic conditions, to yield the corresponding compounds of Formula (I); or (ii) phosgene or a phosgene equivalent, resulting in the corresponding carbamoyl chloride intermediate; or an alkylchloroformate, such as ethyl chloroformate, resulting in the corresponding carbamate, which is reacted with aqueous ammonia, or a substituted amine; which is deprotected by use of anhydrous fluoride $(R_4N^+)F^-$, or under mildly acidic conditions; to yield the corresponding compounds of Formula (I); or (iii) trimethylsilyl isocyanate and deprotected by use of anhydrous fluoride $(R_4N^+)F^-$, or under mildly acidic conditions; to yield the corresponding compounds of Formula (I); or (iv) acetyl chloride in organic solvent which is then deprotected by use of anhydrous fluoride $((R_4N^+)F^-$, or under mildly acidic conditions, to yield the corresponding compounds of Formula (I); or D. reacting a compound of Formula (II) as described above, wherein $B_1$ is tetrahydropyranyl, $C_1$alkyl-$C_{1-3}$alkoxy, or $C_1$alkyl$C_2$alkoxy$C_{1-3}$alkoxy, with (i) sodium or potassium cyanate in an acidic solution, and deprotected by a mild acid treatment, such as pyridinium para-toulenesulphonate in methanol or dilute HCl to yield the corresponding compounds of Formula (I); or (ii) phosgene or a phosgene equivalent, resulting in the corresponding carbamoyl chloride intermediate; or an alkylchloroformate, such as ethyl chloroformate, resulting in the corresponding carbamate, which is reacted with aqueous ammonia, or a substituted amine; and deprotected by a mild acid treatment, such as pyridinium para-toulenesulphonate in methanol or dilute HCl; to yield the corresponding compounds of Formula (I); or (ii) with trimethylsilyl isocyanate, then deprotected by a mild acid treatment, such as pyridinium para-toulenesulphonate in methanol or dilute HCl; to yield the corresponding compounds of Formula (I); or (iii) with acetyl chloride in organic solvent which is then deprotected by a mild acid treatment, such as pyridinium para-toulenesulphonate in methanol or dilute HCl to yield the corresponding compounds of Formula (I); or E. reacting a compound of Formula (II) as described above, wherein $B_1$ is t-butyloxycarbonyl with (i) sodium or potassium cyanate in an acidic solution, and deprotected by treatment with trifluroracetic acid, trimethylsilyltrifilate with 2,6-lutidine, or with anhydrous ether HCl; or (ii) phosgene or a phosgene equivalent, resulting in the corresponding carbamoyl chloride intermediate; or an alkylchloroformate, such as ethyl chloroformate, resulting in the corresponding carbamate, which is reacted with aqueous ammonia, or a substituted amine; and deprotected by treatment with trifluroracetic acid, trimethylsilyltrifilate with 2,6-lutidine, or with anhydrous ether HCl; to yield the corresponding compounds of Formula (I); or (iii) with trimethylsilyl isocyanate and then deprotected, optionally with ethane thiol in the presence of aluminium trichloride by treatment with trifluroracetic acid, trimethylsilyltrifilate with 2,6-lutidine, or anhydrous ether HCl; to yield the corresponding compounds of Formula (I); or (iv) with acetyl chloride in organic solvent which is then deprotected, optionally with ethane thiol in the presence of aluminium trichloride; or by treatment with trifluroracetic acid, trimethylsilyltrifilate with 2,6-lutidine, or anhydrous ether HCl to yield the corresponding compounds of Formula (I); or F. reacting a compound of Formula (II) as described above, wherein $B_1$ is an alkoyl or aroyl with (i) sodium or potassium cyanate in an acidic solution and deprotected with a suitable base, such as potassium carbonate; to yield the corresponding compounds of Formula (I); or (ii) with trimethylsilyl isocyanate and deprotected with a suitable base, such as potassium carbonate; to yield the corresponding compounds of Formula (I); or (iii) with acetyl chloride in organic solvent which is then deprotected by treatment with a suitable base, such as potassium carbonate; to yield the corresponding compounds of Formula (I).

The compounds of Formula (II) can be produced by a process which comprises

A process for producing a compound of the Formula (II) as defined above, which process comprises A. reacting a compound of Formula (III)

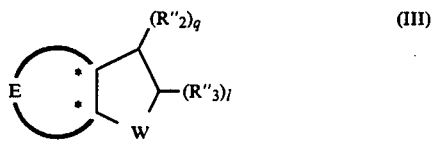

wherein $R''_2$ and $R''_3$ are =O;

W, E, $R_1$, $R_7$, $R_8$, s, q, l, m, n, v, Ar, S, t, and Y are as defined for Formula (II); with hydroxylamine in solvent to yield the corresponding oxime derivative of Formula (IV)

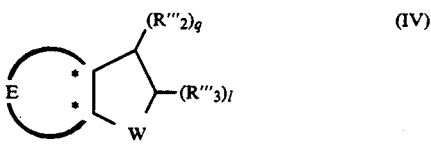

wherein $R'''_2$ and $R'''_3$ are =N—OH;

W, E, $R_1$, $R_7$, $R_8$, s, q, l, m, n, v, Ar, S, X, t, and Y are as defined for Formula (II); which is then reduced with borane pyridine complex, borane trimethylamine, or borane tetrahydrofuran or other borane complexes, to yield the hydroxylamine deriviatives of Formula (II); or B. reacting a compound of Formula (IV) as defined above with sodium cyanoborohydride or phenyldimethylsilane in anhydride in trifluroacetic acid to yield the hydroxylamine deriviatives of Formula (II); or C. reacting a compound of Formula (V)

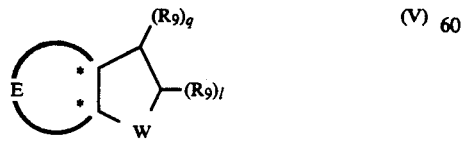

wherein $R_9$ is X';

X' is a leaving group, such as a halogen, tosylate, mesylate or a triflate moiety;

W, E, $R_1$, $R_7$, $R_8$, s, q, l, m, n, v, Ar, S, X, t, and Y are as defined for Formula (II); with Z-furfulaldehyde oxime and base to yield the corresponding nitrone of Formula (VI) which is hydroylzed to yield the corresponding hydroxylamine derviatives of Formula (II);

D. reacting a compound of Formula (V) as described above, with a protected hydroxylamine to yield the corresponding protected hydroxylamine of Formula (II); or E. reacting a compound of the Formula (VI)

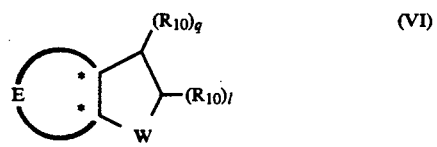

wherein $R_{10}$ is OH;

W, E, $R_1$, $R_7$, $R_8$, s, q, l, m, n, v, Ar, S, X, t, and Y are as defined for Formula (II) as described above; with a protected hydroxylamine, such as N,O-bis(t-butyloxycarbonyl)hydroxylamine) or bisbenzyloxycarbonyl, and triphenylphosophine/diethyldiazodicarboxylate to produce an intermediate which is deprotected, preferably with acid to yield the hydroxylamines of Formula (II).

The present compounds of Formula (I) can be prepared by art-recognized procedures from known compounds. Several synthetic schemes can be used to prepare the compounds of this invention. Although the schemes when illustrated herein utilize only one particular compound, a substituted 1,2,3,4-tetrahydrophenanthren-4-one, it will be easily seen by one skilled in the art, that using the appropriate starting materials other compounds of this invention can be prepared in the same manner. Suitable known and documented starting materials useful in the present invention, include but are not limited to, such ring systems as 1,2,3,4-Tetrahydrophenanthren-4-one; 2,3-Dihydrocyclopenta[b]naphthalen-1-one; 2,3-Dihydrocyclopenta[a]naphthalen-1-one; 1,2-Dihydrocyclopenta[a]naphthalen-3-one; Naphtho[2,3-b]furan-3-one; Naphtho[2,3-b]thiophen-3-one; Naphtho[1,2-b]furan-3-one;

The compounds of Formula (I) can be prepared according to the following synthetic route, as displayed in Scheme I below:

SCHEME I

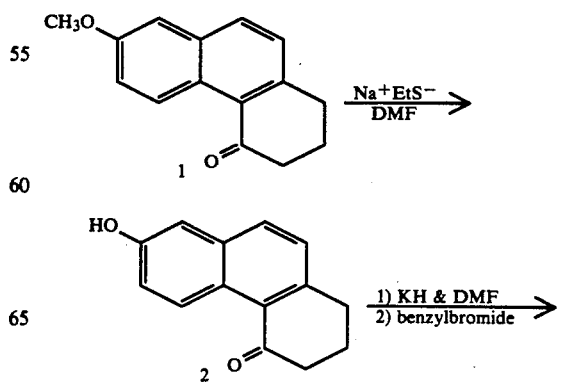

SCHEME I -continued

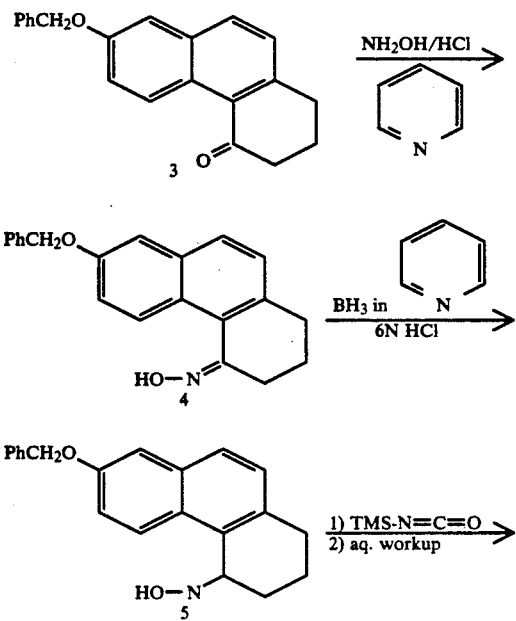

In scheme I, compound 1 or any other suitable alkoxy derivative may be treated by a known means to remove the alkyl portion of the alkoxy group, such as using a solution of sodium ethanethiolate in a solvent, such as dry DMF, to which the alkoxy derivative is added and heated. Following concentration of the reaction and addition of an organic solvent, such as ethyl acetate, an aqueous acidic workup yields the corresponding hydroxy derivative 2. The hydroxy compound 2 is then treated with a metal hydride, such as potassium hydride, and after the gas evolution subsides, a benzylhalide or phenylethyl halide, such benzylbromide, is added. After stirring and concentrating, the residue is dissolved in an organic solvent, such as ethyl acetate, and washed with acid, preferably hydrochloric, to yield after a standard aqueous workup the benzyloxy derivative 3. Compound 3 is then converted to the corresponding oxime 4 by addition of hydroxylamine hydrochloride in a solvent, such as pyridine and heated for about 30 minutes to about 2 hours. The oxime 4 is reduced to the corresponding hydroxylamine 5 by addition of a borane/pyridine complex to which is added, after stirring an acidic solution, preferably 6N HCl. Borane dimethylsulfide in tetrahydrofuran may also be used. Addition of an alkali metal hydroxide, such as NaOH, and extraction into an organic solvent, for example ethyl ether or CH$_2$Cl$_2$, yields the hydroxylamine 5. The hydroxylamine is converted to the corresponding hydroxyurea 6 by addition of trimethysilylisocyanate and heating followed by an aqueous/organic workup.

The hydroxamates can also be produced in a similar manner from the same intermediate 5 which is then converted to a diacetate intermediate by addition of an acylating agent, such as acetyl chloride (about 2 equivalents), with triethylamine (about 3 equivalents) in methylene chloride for about 30 minutes. Acetic anhydride in the presence of other bases such as pyridine will also work. The O-acetate moiety is removed by hydrolysis with an alkali metal hydroxide, such as lithium hydroxide, to yield the corresponding hydroxamic acid of Formula (I). The oxime 4 or O-protected derivatives, such as the acetate, may also be reduced by borane-trimethylamine, borane-tetrahydrofuran, sodium cyanoborohydride in methanol, or other borane compounds.

Another synthetic route to prepare the compounds of Formula (I) is described in Scheme II, illustrated below.

SCHEME II

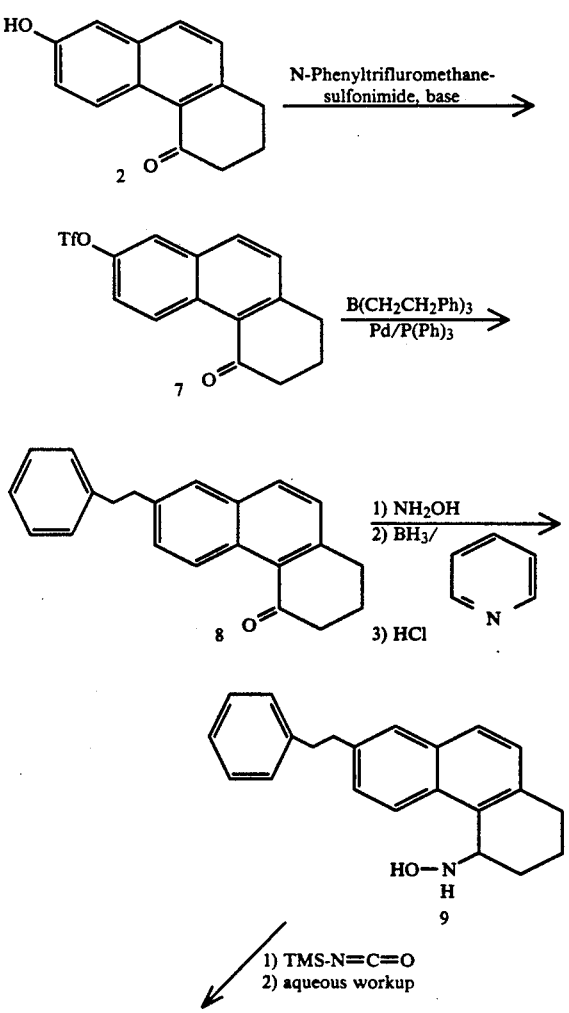

-continued
SCHEME II

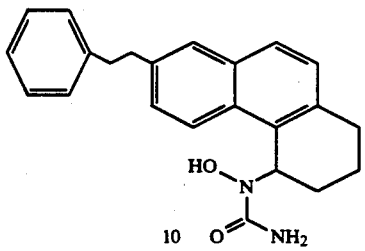

The hydroxytetralone derivative 2 is modified to contain an active leaving group, such as the triflate indicated in 7. Other acceptable leaving groups are the bromides, chlorides, iodides, tosylates, and mesylates. Using a bidentate Pd (II) catalyst, such as $PdCl_2$ (dppf) or $Pd(PPh_3)_4$, or any other acceptable coupling agent, and a tris(phenethyl)borane derivative, using the method of Sukuki (A. Suzuki et. al. J.A.C.S., 111, pgs. 314–321, 1989) results in the addition of the appropriate $R_1$ group to yield the corresponding tetralone compound 8. The above cited procedure is especially useful for the preparation of compounds in which $R_1$ is an alkyl group. The use of other organometallics, such as alkylzinc, -lithium, -tin or -aluminum reagents may also be useful when $R_1$ is an alkyl group (see references cited in Suzuki paper). Additional ways of coupling using a palladium catalysis and organoborane (A. Suzuki, Pure & Appl. Chem., 57, pgs. 1749–1758, 1985), organozinc (R. Keenan et. al., Syn. Commun., 19, pgs. 793–798, 1989), or organotin (J. K. Stille, Angew. Chem. Int. Ed., 25, pgs. 508–524, 1986) compounds may also be useful in this process step when $R_1$ is an aryl or olefinic group. Also potentially useful when $R_1$ is an alkyl, aryl, or olefinic group is the copper mediated coupling of aryl trifaltes, such as 7, using the procedure of McMurry (J. E. McMurry et. al., Tett. Lett., 24, pgs. 2723–2726, 1983). The ketone 8 is converted to the hydroxylamine 9 by reaction with hydroxylamine, and subsequently reduced with borane in pyridine and hydrochloric acid. The hydroxylamine 9 is converted into the corresponding hydroxyurea 10 by the method outlined in Scheme I. The hydroxylamine 9 is also converted into the corresponding hydroxamate by the method outlined above for Scheme I.

Alternatively, the hydroxyureas of Formula (I) wherein $R_4$ is $NR_5R_6$ is a substituted amine or cyclic amine can be prepared by reaction of the appropriately substituted hydroxylamine hydrochloride of Formula (II) with phosgene to yield the acyl chloride intermediate which is reacted with the appropriate amine to yield the compounds of Formula (I).

An additional alternative to the use of phosgene is an alkyl chloroformate, such as ethyl chloroformate, in which case the resulting $R_4$ term of Formula (I) will determine the reaction time and temperature needed for the reaction to proceed, i.e. at 0° C. or below or, if slow at an elevated temperatures of 100°–200° C. in the appropriate solvent.

The preparation of the hydroxyureas of Formula (I) when —OB is a protecting group, as opposed to the free hydroxyl proceeds in a similiar manner. The protected hydroxylamine is reacted with phosgene or a phosgene equivalent, such as carbonyl diimidazole or phosgene trimer yielding a protected hydroxylamine intermediate which is reacted with an appropriate amine component ($NHR_5R_6$) to yield the protected hydroxyurea of Formula (I). Alternatively, the reaction of the protected hydroxylamine with trimethylsilyl isocyante or with sodium or potassium cyanate in an acidic solution as discussed above may be employed to prepare the protected hydroxyurea of Formula (I). This is followed by any means appropriate for the deprotection of the —$OB_1$ group. Deprotection of the hydroxyl may be by hydrogenation with $H_2$/Pd/C when D is benzyl, by mild acid treatment, such pyridinium para-toluenesulphonate in refluxing methanol or dilute HCl when $B_1$ is tetrahydropyranyl, by a suitable base, such as potassium carbonate when D is an alkoyl or aroyl, by use of anhydrous fluoride $(R_4N^+)F^-$ when D is $Si(R_x)_3$, or by treatment with trifluoroacetic acid, trimethylsilyltriflate and 2,6-lutidine, or anhydrous ether HCl when $B_1$ is t-butyloxycarbonyl. In general, suitable protecting groups and methods for their removal will be found in T. W. Greene, Protective Groups in Organic Synthesis, Wiley, N.Y., 1981.

A hydroxylamine which is protected, such as O-benzylhydroxylamine or O-tetrahydropyranyl hydroxylamine, or other O-protected hydroxylamines can also be used to produce the hydroxyureas of Formula (I) using as a starting material a compound having an active leaving group X (in structure 11, Scheme III replace OH with X'), such as Cl, Br, OMs, or OTs by reaction with the hydroxylamine ($NH_2$-$OB_1$) with heating in an appropriate solvent to yield a protected intermediate of Formula (II). The protected intermediate may then be deprotected using the standard removal conditions for the protecting group employed to yield the free hydroxylamines of Formula (II), or the protected intermediate may used as outlined above to prepare the O-protected hydroxyurea and then deprotected to yield the final compounds of Formula (I). Similarly, the above noted process can be used to make the starting amine compounds, chiral or not as so desired, by use of $NH_3$, or $N_3$ and suitable reduction step, all well known to those skilled in the art.

The starting compound, a halo compound can readily be prepared from the mesylate or toyslate derivatives (benzylic sulfonates are highly reactive and thus in most cases are used as non-isolated intermediates) or can be produced directly by a number of art known procedures from the corresponding alcohol. The mesylates or tosylate derivatives can be prepared from the ketone derivatives by reduction to the corresponding alcohol by any number of readily available agents, such as sodium borohydride, or lithium aluminum hydride. The alcohol is then reacted with mesyl or tosyl chloride in the presence of an appropriate base, for example pyridine or triethylamine, with or without additional solvent to form the mesylate or tosylate derivatives which are in turn displaced, for example either by in situ reaction or in a subsequent reaction with lithium chloride or bromide in acetone, to form the corresponding halogenated derivatives.

Selected examples of protected compounds of Formula (II) may also prepared by reaction of the alcohol 11 with a protected hydroxylamine, such as O-benzyl hydroxylamine or O-t-butyldiphenylsilyl hydroxylamine under solvolytic conditions, for example in the presence of trifluoroacetic acid. (A. O. Stewart et al., J. Org. Chem., 54, 1221–1223 (1989). The protected intermediate may then be deprotected using the standard removal conditions for the protecting group employed to yield the free hydroxylamines of Formula (II), or the protected intermediate may be converted first to the protected urea and then to the final compounds of Formula (I) as discussed above.

Another synthetic pathway which will produce the hydroxylamines of Formula (II) and may also used to prepare the optically active intermediates, if the optically active alcohol derivative is used as a starting material is illustrated in Scheme III below. The alcoholic starting material 11 is treated with N,O-bis(t-butyloxycarbonyl)hydroxylamine and triphenylphosphine/diethyldiazodicarboxylate (DEAD) producing the intermediate 12 which is then treated with an appropriate acid, such as trifluroacetic acid or hydrochloric acid, to produce the free hydroxylamines of Formula (II). The optically active alcohol 11 may be prepared by enantioselective reduction of the corresponding ketone precursor with an appropriate reducing agent (M. Kawasaki et. al., *Chem. Pharm. Bull.*, 33, pgs 52–60, 1985 or D. Mathre et. al., *J. Org. Chem.*, 56, pgs 751–762 and references cited therein). The thus obtained optically active alcohol may also be converted to the corresponding optically active halo or sulfonate compound (see D. Mathre, compounds of Formula (II). Such steps as noted above are obviously useful as well to make the racemic mixture.

The alcoholic starting material 11 is treated with diphenylphosphoryl azide and triphenylphosphine/diethyldiazodicarboxylate (DEAD) producing the optically active azide which can be reduced to the optically active amine 13.

SCHEME III

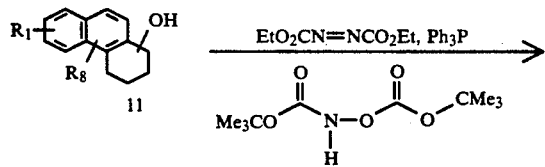

-continued
SCHEME III

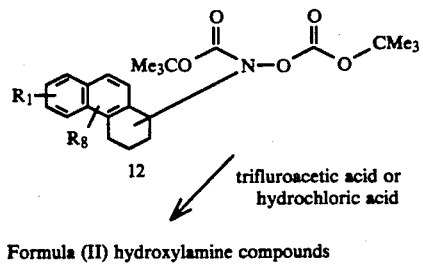

Formula (II) hydroxylamine compounds

An additional route for preparation of the optically active compounds of Formula (I) is detailed in Scheme IV below. The sequence starts with optically active amines, obtained through a variety of methods including the classical methods of preparing salts with chiral acids, such as camphor sulfonic acids, such techniques being readily apparent to those skilled in the art. The requisite racemic amine can be prepared from the alcohol 11 or activated derivatives thereof, by the methods previously outlined above, substituting ammonia for (un)substituted hydroxylamines. One available review for resolving racemic compounds is by R. M. Secor, *Chem. Rev.*, 63, 197 (1963). The starting material 13 is either the pure "R" or a pure "S" configuration which is then reacted to form the intermediate 14 with 4-methoxybenzaldehyde in triethylamine. The intermediate 14 is then oxidized by a variety of agents, such as MCPBA (metachloroperbenzoic acid), MPP (monoperoxyphthalate) or MMPP (magnesium monoperoxyphthalate) to yield the oxaziridine derivative 15 which under acidic conditions then yields the hydroxylamine salt 16. The general procedure can be found in Polanski et al., *Tetrahedron Letters.*, 28, 2453–2456 (1974). Alternatively, the optically active amine 13 may be converted directly to the chiral hydroxylamine 16 using dimethyldioxirane (Danishesky, et. al. *J. Org. Chem.*, vol. 55, p 1981–1983, 1990) or a peracid anhydride, such as benzoyl peroxide (R. M. Coates et. al., *J. Org. Chem.*, vol. 55, 3464–3474, 1990).

SCHEME IV

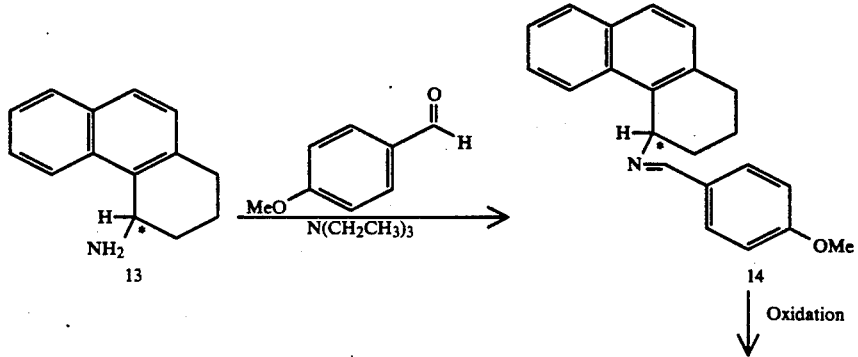

-continued
SCHEME IV

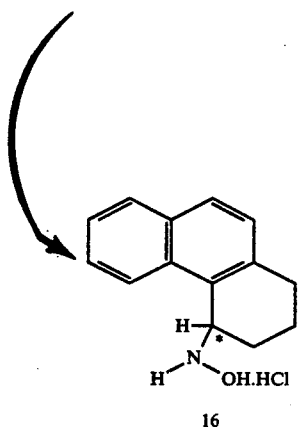

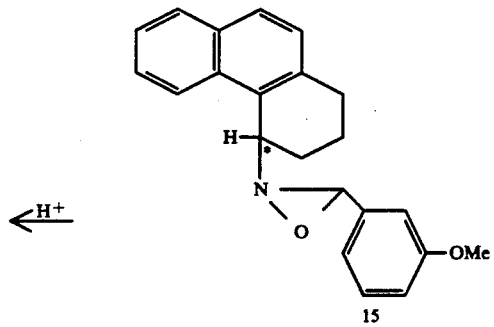

An additional method for obtaining the homochiral hydroxyureas of Formula (I) is to form diastereomeric adducts of the racemic hydroxyureas or hydroxamates which may then be separated by a variety of commonly used techniques, including flash chromatography and HPLC. This approach is illustrated in Scheme V below. Reaction with a homochiral oxazolidinone, for example 4-(phenylmethyl)-2-oxazolidinone (see *Org. Syn.*, John Wiley & Sons, Inc., vol. 68, p 77 for preparation), with phosgene or a phosgene equivalent, such as phosgene trimer or carbonyl diimidazole, and a base in an anhydrous solvent, preferably with NaH in toluene at reflux and then adding to to this cooled solution at about −70° C. to about 20° C., preferably about −30° to about 0° C. for use with phosgene. Should a phosgene equivalent be used, the temperature range will be from about 20° C. to about 200° C. The thus formed intermediate, for example, when phosgene is used, a chloro carbamate may be isolated.

Additional 4-substituted chiral oxazolidinones which may also be used are optionally substituted (R groups) aryl, arylmethyl, heteroaryl, or heteroarylmethyl wherein the substituents include, but are not limited to, mono or disubstituted alkyl, halo, alkoxy, cyano, or any other protected amino, alcohol, carboxy, or sulfur (regardless of oxidation state). Additionally R can be an alkyl moiety of greater than 2 carbons, preferably longer, such as t-butyl or isopropyl, which may be optionally substituted as well. Representative examples of the aryl and heteroaryl groups include, but not limited to phenyl, naphthyl, pyrrolyl, thienyl, thiazinyl and furanyl. These oxazolidinones are prepared from the chiral amino alcohols which are readily available from reduction of the chiral amino acids by the general procedure of Evans (*Org. Syn.*, John Wiley & Sons, Inc. Vol. 68, p 77 and references cited therein) which are incorporated by reference herein.

Addition of this adduct to a solution containing the hydroxyurea in a chloronated hydrocarbon or etheral solvent, preferably $CH_2Cl_2$, and a base (either an amine base such as trialkylamine or pyridine or a solid alkali metal carbonate, such as potassium or calcium, but most preferably triethylamine) affords the diastereomeric adducts, 17A and 17B. Chromatography or other physical methods are employed to separate these adducts which are then cleaved under basic conditions, for example using an alkali metal hydroperoxide, such as lithium, in an aqueous-etheral solvent (THF, glyme, digylme, ethyl ether) at about −20 to about 50° C., preferably from about −5° C. to about room temperature, more preferably from about 0° C. to about 15° C. to yield the individual enantiomers of the hydroxyurea.

SCHEME V

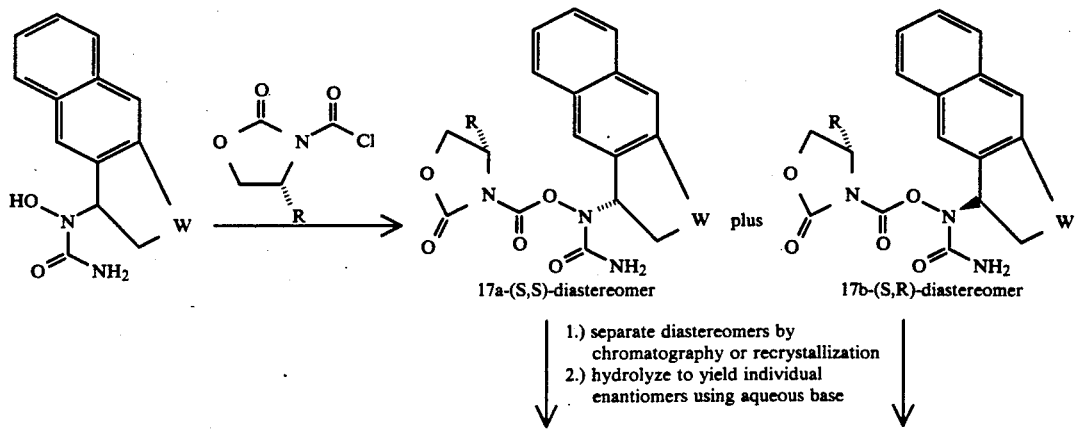

SCHEME V -continued

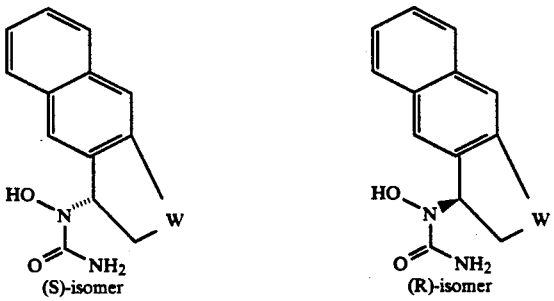

(S)-isomer      (R)-isomer

For the preparation of compounds in which W contains nitrogen a synthetic sequence similar to that outlined in Scheme I is employed (illustrated in Scheme VI). The starting materials 18 shown in Scheme VI can be prepared by the method of Kano et al (*J. C. S. Perkin I*, pgs 2105-2111, 1980 or Bradley et al., *J. C. S. Perkin I*, pgs 2019-2023 (1972) and references therein) or when $R_1$=OMe by dealkylation/refunctionalization as described in previous examples (Schemes I and II). When $R_2$ is alkyl or substituted alkyl, this group is attached by reaction of 18 using the appropriate base catalysis and alkylating reagent. When $R_2$ in the final product 20 is to be hydrogen, then protection of 18 by formation of the carbamate 19 is required ($R_2$=CO$_2R_3$). Following transformation to the protected hydroxyurea 20, the nitrogen is deprotected, for example with acid or fluoride when $R_3$ is t-butyl or trimethylsilylethyl respectively. Enantiomerically pure compounds can be prepared from 19 using the procedures outlined above (Schemes III and IV plus text) or from 20 ($R_3$=alkyl or substituted alkyl or COR$_3$) by resolution (Scheme V).

SCHEME VI

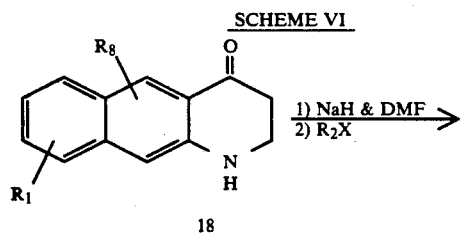

18

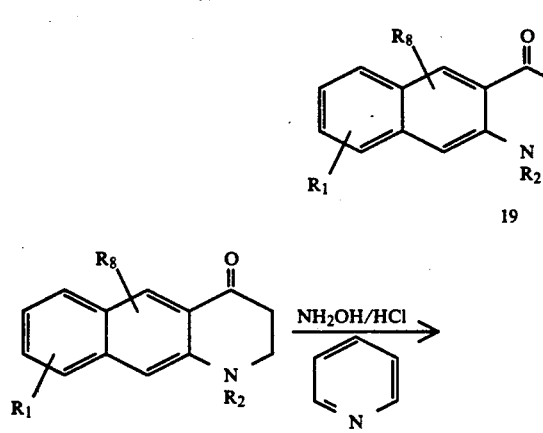

19

-continued SCHEME VI

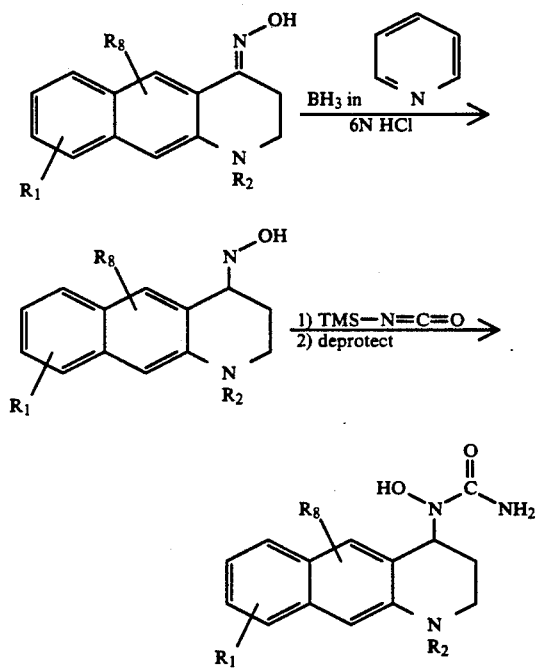

20

$R_2$ = alkyl, substituted alkyl or CO$_2R_3$ where $R_3$ is t-butyl or trimethylsilylethyl Compounds in which q=0 and l=1 (Formula (I)) can be prepared by the 1,2 carbonyl transposition of the ketone intermediates used to prepare compounds in which q=1 and l=0 (Scheme VII). Many such 1,2 carbonyl transposition procedures are known (see *Tetrahedron*, 39, p 345, 1983 for review). A particularly useful and general procedure is the reduction, dehydration, hydroboration-oxidation sequence (see Kirkiacharian, B. S. et. al., *Synthesis*, p 815, 1990 for hydroboration-oxidation). When W contains nitrogen, suitable protection is required to effect this transformation. Protecting groups such as those previously outlined are applicable. When W is sulfur the oxidation of the borane to the ketone may afford sulfur oxidation products, sulfoxide or sulphones. In cases where selective reduction of the oxidized sulfur is not possible alternative routes are employed.

Scheme VII

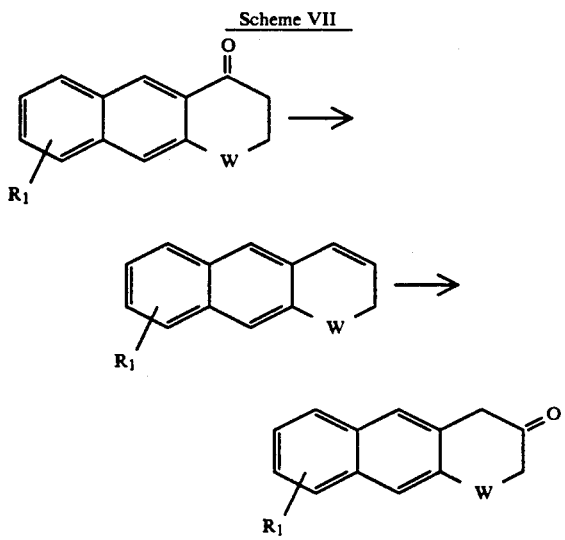

Pharmaceutically acceptable base addition salts and their preparation are well known to those skilled in pharmaceuticals. Pharmaceutically acceptable bases (cations) of the compounds of Formula (I) which are useful in the present invention include, but are not limited to, nontoxic organic and inorganic bases, such as ammonium hydroxide, arginine, organic amines such as triethylamine, butylamine, piperazine and (trihydroxy)-methylamine, nontoxic alkali metal and alkaline earth metal bases, such as potassium, sodium and calcium hydroxides. Pharmaceutically acceptable acid addition salts of the compounds of Formula (I) which are useful in the present invention include, but are not limited to, maleate, fumarate, lactate, oxalate, methanesulfonate, ethane-sulfonate, benzenesulfonate, tartrate, citrate, hydrochloride, hydrobromide, sulfate and phosphate salts and such salts can be readily prepared by known techniques to those skilled in the art.

METHOD OF TREATMENT

It has now been discovered that the compounds of Formula (I) are useful for treating disease states mediated by the lipoxygenase pathway of arachidonic acid metabolism, specifically the 5-lipoxygenase enzyme, in an animal, including mammals, in need thereof. The discovery that the compounds of Formula (I) are inhibitors of the 5-lipoxygenase pathway is based on the effects of the compounds of Formula (I) on the production of 5-lipoxygenase products in blood ex vivo and on the 5-lipoxygenase in vitro assays, some of which are described hereinafter. The 5-lipoxygenase pathway inhibitory action of the compounds of Formula (I) was confirmed by showing that they impaired the production of 5-lipoxygenase products such as leukotriene B$_4$ production by RBL-1 cell supernatants.

The pathophysiological role of arachidonic acid metabolites has been the focus of recent intensive studies. In addition to the well-described phlogistic activity (i.e. general inflammatory activity) of prostaglandins, the more recent description of similar activity for other eicosanoids, including the leukotrienes, has broadened the interest in these products as mediators of inflammation [See, O'Flaherty, Lab. Invest., 47, 314-329 (1982)]. The reported discovery of potent chemotactic and algesic activity for LTB$_4$ [see, Smith, Gen. Pharmacol., 12, 211-216 (1981) and Levine et al., Science, 225, 743-745 (1984)], together with known LTC$_4$ and LTD$_4$-mediated increase in capillary permeability [see, Simmons et al., Biochem. Pharmacol., 32, 1353-1359 (1983), Vane et al., Prostaglandins, 21, 637-647 (1981), and Camp et al., Br. J. Pharmacol., 80, 497-502 (1983)], has led to their consideration as targets for pharmacological intervention in both the fluid and cellular phases of inflammatory diseases.

The pharmacology of several inflammatory model systems has attested to the effectiveness of corticosteriods in reducing the cellular infiltration. These results, and the observation that corticosteriods inhibit the generation of both cyclooxygenase and lipoxygenase products, suggest that such dual inhibitors may effectively reduce both the fluid and cellular phases of the inflammatory response since selective cyclooxygenase inhibitors do not reliably inhibit cell influx into inflammatory sites [See, Vinegar et al., Fed. Proc., 35, 2447-2456 (1976), Higgs et al., Brit. Bull., 39, 265-270 (1983), and Higgs et al., Prostaglandins, Leukotrienes and Medicine, 13, 89-92 (1984)]. Under optimal conditions, it is likely that an agent with preferential lipoxygenase inhibitory activity would not share the ulcerogenic liability of cyclooxygenase inhibitors or the toxicity of corticosteroids. This may suggest that the compounds of the present invention could be useful in treating diseases, such as osteoarthritis, where it is beneficial to limit ulcerogenic activity or steroidal side effects. [See Palmoski et al., "Benoxaprofen Stimulates Proteoglycan Synthesis in Normal Canine Knee Cartiledge in Vitro," Arthritis and Rheumatism 26, 771-774 (1983) and Rainsford, K. D., Agents and Actions 21, 316-319 (1987).]

Clinical data supports the enthusiasm for inhibitors of the 5-lipoxygenase pathway in a variety of inflammatory diseases in which granulocyte and/or monocyte infiltration is prominent. The reported demonstration of elevated levels of LTB$_4$ in rheumatoid arthritic joint fluid [See, Davidson et al., Ann. Rheum. Dis., 42, 677-679 (1983)] also suggests a contributing role for arachidonic acid metabolites in rheumatoid arthritis. Sulfasalazine, which is used for treatment of ulcerative colitis, has been reported to inhibit LTB$_4$ and 5-HETE production in vitro [See, Stenson et al., J. Clin. Invest., 69, 494-497 (1982)]. The recently reported preliminary observation of efficacy, including remission, reported with sulfasalazine treatment of rheumatoid arthritic patients [See Neumann et al., Brit. Med. J., 287, 1099-1102 (1983)] illustrates the utility of inhibitors of the 5-lipoxygenase pathway in rheumatoid arthritis.

Additionally it has been reported that inflamed gastrointestinal mucosa from inflammatory bowel disease patients showed increased production of LTB$_4$ [See, Sharon et al., Gastroenterol., 84, 1306 (1983)], which suggests that sulfasalazine can be effective by virtue of inhibition of production of chemotactic eicosanoids (such as the 5-lipoxygenase pathway product known as LTB$_4$). The observations serve to underscore utility of inhibitors of the 5-lipoxygenase pathway in inflammatory bowel disease.

Another area of utility for an inhibitor of the 5-lipoxygenase pathway is in the treatment of psoriasis. It was demonstrated that involved psoriatic skin had elevated levels of LTB$_4$ [See, Brain et al., Lancet, 19, Feb. 19, 1983]. The promising effect of benoxaprofen on psoriasis [See, Allen et al., Brit. J. Dermatol., 109, 126-129 (1983)], a compound with in vitro lipoxygenase inhibitory activity lends support to the concept that inhibitors of the 5-lipoxygenase pathway can be useful in the treatment of psoriasis.

Lipoxygenase products have been identified in exudate fluids from gouty patients. This disorder is characterized by massive neutrophil infiltration during the acute inflammatory phases of the disease. Since a major 5-lipoxygenase product, $LTB_4$, is produced by neutrophils, it follows that inhibition of the synthesis of $LTB_4$ may block an amplification mechanism in gout.

Another area in which inhibitors of the 5-lipoxygenase product can have utility is in myocardial infarction. Studies in dogs with the dual inhibitor, BW755-C, demonstrated that the area of infarction following coronary occlusion was reduced, and such reduction was attributed to inhibition of leukocyte infiltration into the ischaemic tissue [See, Mullane et al., *J. Pharmacol. Exp. Therap.*, 228, 510–522 (1984)].

Yet another area in which inhibitors of lipid peroxidation involved in the OPUFA mediated can have utility is that generally referred as degenerative neurological disorders, such as Parkinson's disease. Another area is that of traumatic or ischemic injuries, such as stroke, brain or spinal cord injuries and inflammatory disease of the brain and spinal column. More specifically preferred disease states are the mycardial induced ischemic injuries and/or reperfusion injuries. [See, Braughler et al., *Jour. Biol. Chem.*, Vol. 262, No. 22, pp10438–40 (1987), see also Xu et al., *J. Neurochemistry*, 55, 907–912 (1990); Asano et al., *Molecular and Chemical Neuropathology*, 10: 101–133 (1989) and Bracken et al., *NE. J. Med.*, 322: 1405–1411 (1990)].

Yet another area of utility for inhibitors of the 5-lipoxygenase pathway is in the area of prevention of rejection of organ transplants. [See, e.g., Foegh et al., *Adv. Prostaglandin, Thromboxane, and Leukotriene Research*, 13, 209–217 (1983).]

Yet another utility for inhibitors of the 5-lipoxygenase pathway is in the treatment of tissue trauma. [See, e.g., Denzlinger et al. Science, 230 (4723), 330–332 (1985)].

Furthermore, another area of utility for inhibitors of the 5-lipoxygenase pathway is in the treatment of inflammatory reaction in the central nervous system, including multiple sclerosis. [See, e.g., Mackay et al., *Clin. Exp. Immunology*, 15, 471–482 (1973)].

Another area of utility for inhibitors of the 5-lipoxygenase pathway is in the treatment of asthma. [See, e.g., Ford-Hutchinson, *J. Allergy Clin. Immunol.*, 74, 437–440 (1984)]. Additionally another utility for inhibitors of the 5-lipoxygense pathway is in the treatment of Adult Respitory Distress Syndrome. [See, e.g., Pacitti et. al., *Circ. Shock*, 21, 155–168 (1987)]. Yet another utility for inhibitors of the 5-lipoxygenase pathway is in the treatment of allergic rhinitis.

Another area of utility for inhibitors of the 5-lipoxygenase pathway is in the treatment of vasculitis, glomerulonephritis, and immune complex disease. [See Kadison et al., "Vasculitis: Mechanism of Vessel Damage" in *Inflammation; Basic Principles and Clinical Correlates*, 703–718, Ed. Gallin et al., Raven Press, New York, N.Y. (1988).]

Another area of utility for inhibitors of the 5-lipoxygenase pathway is in the treatment of dermatitis. [See Pye et al., "Systemic Therapy" in *Textbook of Dermatology*, Vol. III, 2501–2528, Ed. Rook et al., Blackwell Scientific Publications, Oxford, England (1986).]

Another area of utility for inhibitors of the 5-lipoxygenase pathway is in the treatment of atherosclerosis.

Recent studies have shown that inhibition of oxidative modification of low density lipoprotein slows progression of atherosclerosis, and that inhibitors of lipoxygenase effectively inhibit cell-induced oxidative modification. [See Carew et al., *Proc. Natl. Acad. Sci. USA*, 84, 7725–7729, November 1987; and Steinberg, D., *Cholesterol and Cardiovascular Disease*, 76, 3, 508–514 (1987).]

An additional area of utility for inhibitors of the 5-lipoxygenase pathway is in the opthamalogic area, in particular general inflammation of the corneal anterior and posterior segments due to disease or surgery such as in post surgical inflammation, uveitis, and allergic conjuntivitis. [See Rao N. et al. *Arch. Ophathmal.* 105 (3) 413–419 (1987); Chiou, L. and Chiou, G. *J. Ocular Pharmacol.* 1, 383–390 (1985); Bazan H. *J. Ocular Pharma*, 4, 43–49 (1988); and Verbey N. L. et al., *Current Eye Research* 7, 361–368 (1988).]

FORMULATION OF PHARMACEUTICAL COMPOSITIONS

The compounds of this invention are administered in conventional dosage forms prepared by combining a compound of Formula (I) or (II) ("active ingredient") in an amount sufficient to produce 5-lipoxygenase pathway inhibiting activity with standard pharmaceutical carriers or diluents according to conventional procedures. These procedures may involve mixing, granulating and compressing or dissolving the ingredients as appropriate to the desired preparation. The description of formulations, dosage, and administrations of the compounds of this invention as used herein apply to both the compounds of Formulas (I) and Formula (II).

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Preferably, each parenteral dosage unit will contain the active ingredient [i.e., the compound of Formula (I)] in an amount of from about 30 mg. to about 300 mg. Preferably, each oral dosage will contain the active ingredient in an amount of from about 50 mg to about 1000 mg.

The compounds of Formula (I) may also be administered topically to a mammal in need of the inhibition of the 5-lipoxygenase pathway of arachidonic acid metabolism. Thus, the compounds of Formula (I) may be administered topically in the treatment or prophylaxis of inflammation in an animal, including man and other mammals, and may be used in the relief or prophylaxis of 5-lipoxygenase pathway mediated diseases such as rheumatoid arthritis, rheumatoid spondylitis, osteoarthritis, gouty arthritis and other arthritic conditions, inflamed joints, eczema, psoriasis or other inflammatory skin conditions such as sunburn; inflammatory eye conditions including conjunctivitis; pyresis, pain and other conditions associated with inflammation.

The amount of a compound of Formula (I) required for therapeutic effect on topical administration will, of course, vary with the compound chosen, the nature and severity of the inflammatory condition and the animal undergoing treatment, and is ultimately at the discretion of the physician. A suitable anti-inflammatory dose for topical administration is from about 0.5 mg to about 500 mg, the preferred dosage being from about 1 mg to 100 mg, and more preferably from about 5 mg to about 25 mg being administered two or three times daily.

By topical administration is meant non-systemic administration and includes the application of a compound of Formula (I) externally to the epidermis, to the buccal cavity and instillation of such a compound into the ear, eye and nose, and where the compound does not significantly enter the blood stream. By systemic administration is meant oral, intravenous, intraperitoneal and intramuscular administration.

While it is possible for an active ingredient to be administered alone as the raw chemical, it is preferable to present it as a pharmaceutical formulation. The active ingredient may comprise, for topical administration, from 0.01% to 10% w/w, e.g. from 1% to 2% by weight of the formulation although it may comprise as much as 10% w/w but preferably not in excess of 5% w/w and more preferably from 0.1% to 1% w/w of the formulation.

The topical formulations of the present invention, both for veterinary and for human medical use, comprise an active ingredient together with one or more acceptable carrier(s) therefor and optionally any other therapeutic ingredient(s). The carrier(s) must be 'acceptable' in the sense of being compatible with the other ingredients of the formulation and not deleterious to the recipient thereof.

Formulations suitable for topical administration include liquid or semi-liquid preparations suitable for penetration through the skin to the site of inflammation such as: liniments, lotions, creams, ointments or pastes, and drops suitable for administration to the eye, ear or nose.

Drops according to the present invention may comprise sterile aqueous or oily solutions or suspensions and may be prepared by dissolving the active ingredient in a suitable aqueous or alcholic solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98°-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as steric or oleic acid together with an alcohol such as propylene glycol. The formulation may incorporate any suitable surface active agent such as an anionic, cationic or non-ionic sulfactant such as sorbitan esters or polyoxyethylene derivatives thereof. Suspending agents such as natural gums, cellulose derivatives or inorganic materials such as silicaceous silicas, and other ingredients such as lanolin, may also be included.

The compounds of Formula (I) may also be administered by inhalation. By "inhalation" is meant intranasal and oral inhalation administration. Appropriate dosage forms for such administration, such as an aerosol formulation or a metered dose inhaler, may be prepared by conventional techniques. The dosage amount of a compound of Formula (I) administered by inhalation is from about 0.05 mg to about 50 mg, preferably from about 1 mg to about 10 mg administered per day.

This invention relates to a method of treating a disease state which is mediated by the 5-lipoxygenase pathway in an animal in need thereof, including humans and other mammals, which comprises administering to such animal an effective, 5-lipoxygenase pathway inhibiting amount of a Formula (I) compound. This invention further relates to a method of treating analgesia in an animal in need thereof, which comprises administering to such animal an effective, analgesia inhibiting amount of a compound of Formula (I).

By the term "treating" is meant either prophylactic or therapeutic therapy. By the term "mediated" is meant caused by or exacerbated by. Such Formula (I) compound can be administered to such mammal in a conventional dosage form prepared by combining the Formula (I) compound with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. The Formula (I) compound is administered to an animal in need of inhibition of the 5-lipoxygenase pathway in an amount sufficient to inhibit the 5-lipoxygenase pathway. The route of administration may be oral, parenteral, by inhalation or topical.

The term parenteral as used herein includes intravenous, intramuscular, subcutaneous, intra-rectal, intravaginal or intraperitoneal administration. The subcutaneous and intramuscular forms of parenteral administration are generally preferred.

It will be recognized by one of skill in the art that the optimal quantity and spacing of individual dosages of a Formula (I) or (II) compound will be determined by the nature and extent of the condition being treated, the form, route and site of administration, and the particular animal being treated, and that such optimums can be determined by conventional techniques. It will also be appreciated by one of skill in the art that the optimal course of treatment, i.e., the number of doses of the Formula (I) compound given per day for a defined number of days, can be ascertained by those skilled in the art using conventional course of treatment determination tests.

EXAMPLES

Without further elaboration, it is believed that one skilled in the art can, using the preceding description, utilize the present invention to its fullest extent. The following examples further illustrate the synthesis and use of the compounds of this invention. The following examples are, therefore, to be construed as merely illustrative and not a limitation of the scope of the present invention in any way.

SYNTHESIS EXAMPLES

EXAMPLE 1

N-1-(1,2,3,4-Tetrahydrophenanthrenyl)-N-hydroxyurea 1,2,3,4-Tetrahydrophenanthren-1-one oxime. To a solution of 1,2,3,4-tetrahydrophenanthren-1-one (1.0 g, 5.1 mmol) in pyridine was added hydroxylamine hydrochloride (0.69 g, 10.0 mmol). The resulting mixture was stirred at room temperature overnight. The solvent was removed in vacuo. Water was added to the residue, which was then filtered and dried to provide the oxime.

N-1-(1,2,3,4-Tetrahydrophenanthrenyl)-N-hydroxyamine. To a solution of 1,2,3,4-tetrahydrophenanthren-1-one oxime (211 mg, 1.0 mmol) in ethanol at 5° C. was added $BH_3$.pyridine, followed by 10% HCl (3 mL). The resulting mixture was allowed to warm to room temperature and stirred overnight. Additional $BH_3$.pyridine was added, followed by the dropwise addition of 10% HCl (3-6 mL), and the mixture was stirred for another 8 h. Analysis by thin layer chromatography indicated that the reaction was complete, and 10% HCl was added dropwise. The mixture was stirred until the effervescence ceased, and the pH was adjusted to 9-10 with 3N NaOH. Water was added, and the mixture was stirred for 1 h. The solid which formed was removed by filtration, washed with $H_2O$ and dried (150 mg, 61%).

250 MHz $^1$H NMR (CDCl$_3$): δ8.00 (dd, 1H); 7.80 (m, 1H); 7.69 (d, 1H); 7.46 (m, 3H); 4.20 (t, 1H); 3.58 (br s, 2H); 3.25 (dt, 1H); 2.98 (m, 1H); 2.32 (m, 1H); 2.18-1.78 (m, 3H).

N-1-(1,2,3,4-Tetrahydrophenanthrenyl)-N-hydroxyurea. To a solution of N-1-(1,2,3,4-tetrahydrophenanthrenyl)-N-hydroxyamine (147 mg, 0.69 mmol) in THF (15 mL) was added trimethylsilyl isocyanate (0.21 mL, 1.5 mmol). The resulting mixture was heated to reflux for 1 h and then allowed to cool to room temperature. Aqueous NH$_4$Cl was added, and the mixture was partitioned between H$_2$O and EtOAc. The organic extract was washed with H$_2$O and saturated aqueous NaCl and dried (MgSO$_4$). The solvent was removed in vacuo, and the residue was triturated with Et$_2$O to provide the product as a white crystalline solid. (m.p. 192°-193° C.)

250 MHz $^1$H NMR (CDCl$_3$): δ8.00 (dd, 1H); 7.80 (m, 1H); 7.69 (d, 1H); 7.53-7.41 (m, 3H); 5.62 (br t, 1H); 3.22-3.01 (m, 2H); 2.25 (m, 1H); 2.10 (m, 2H); 1.93 (m, 1H).

CIMS (NH$_3$); m/e (rel. int.): 257 [(M+H)+100]; 241 (24); 181 (36).

EXAMPLE 2

N-{3-(2,3-Dihydronaphtho[1,2-b]furyl}-N-hydroxyurea 2-(1-Naphthoxy)acetic acid. To a solution of potassium hydroxide (2.98 g, 52.1 mmol) in H$_2$O (35 mL) was added 1-naphthol (3.08 g, 21.4 mmol), followed by 2-chloroacetic acid (2.32 g, 24.7 mmol). The resulting mixture was heated at reflux for 3 h, then allowed to cool and extracted with EtOAc. The aqueous phase was made acidic by the addition of 3N HCl and extracted with EtOAc. The organic phase from the acidic extraction was washed with saturated aqueous NaCl. The solvent was removed in vacuo to provide the title compound (2.78 g, 64%).

2,3-Dihydronaphtho[1,2-b]furan-3-one. To a solution of 2-(1-naphthoxy)acetic acid (2.26 g, 11.2 mmol) in benzene (20 mL) was added oxalyl chloride (5 mL, 57.3 mmol). The resulting mixture was heated at reflux for 30 min, then allowed to cool and concentrated under reduced pressure. The residue was dissolved in benzene, and to this was added aluminium chloride (1.83 g, 13.9 mmol). The resulting mixture was stirred at room temperature for 1 h, then poured into ice. The organic phase was separated and washed with saturated aqueous NaCl. Removal of the solvent in vacuo provided the title compound (1.74 g, 84%).

2,3-Dihydronaphtho[1,2-b]furan-3-one, oxime. To a solution of 2,3-dihydronaphtho[1,2-b]furan-3-one (1.74 g, 9.5 mmol) in pyridine (50 mL) was added hydroxylamine hydrochloride (1.31 g, 18.9 mmol). The resulting mixture was heated at 70° C. for 4 h, then allowed to cool to room temperature. Water was added to the reaction mixture, and the solid which formed was collected by filtration to provide the title compound (1.57 g, 83%).

$^1$H NMR (CDCl$_3$/MeOH-d$_4$): δ8.05 (m, 1H); 7.85 (m, 1H); 7.64-7.41 (m, 4H); 5.38 (s, 2H).

N-{3-(2,3-Dihydronaphtho[1,2-b]furyl}-N-hydroxyamine. To a solution of 2,3-dihydronaphtho[1,2-b]furan-3-one, oxime (101 mg, 0.51 mmol) in EtOH (4 mL) was added BH$_3$.pyridine (5 mL, 49.5 mmol) and the resulting mixture was allowed to stir at room temperature. Three N HCl (25 mL) was added dropwise over 2 h. Ether was added to the reaction mixture, and the pH was adjusted to basic by the addition of solid Na$_2$CO$_3$. The organic phase was washed with saturated aqueous NaCl concentrated in vacuo to provide the title compound (72 mg, 71%).

$^1$H NMR (CDCl$_3$/MeOH-d$_4$): δ7.99 (m, 1H), 7.82 (m, 1H); 7.50-7.35 (m, 4H); 4.89 (m, 2H); 4.74 (dd, 1H).

N-{3-(2,3-Dihydronaphtho[1,2-b]furyl}-N-hydroxyurea. To a solution of N-{3-(2,3-dihydronaphtho[1,2-b]furyl}-N-hydroxyamine (72 mg, 0.36 mmol) in THF (4 mL) was added trimethylsilylisocyanate (98 μL, 0.72 mmol). The resulting solution was heated at 60° C. for 1 h, then allowed to cool and concentrated under reduced pressure. The residue was dissolved in EtOAC and washed successively with H$_2$O and saturated aqueous NaCl. The solvent was removed in vacuo, and the residue was triturated with Et$_2$O. The solid residue was purified by flash chromatography, eluting with 3% MeOH/CH$_2$Cl$_2$ and recrystallized from MeOH/CH$_2$Cl$_2$ to provide the title compound (31 mg, 35%). m.p. 191°-192° C.

$^1$H NMR (CDCl$_3$/MeOH-d$_4$): δ7.96 (m, 1H); 7.82 (m, 1H); 7.52-7.38 (m, 4H); 6.20 (dd, 1H); 4.80 (m, 2H).

CIMS (NH$_3$); m/e (rel. int.): 262 (5), 246 (4), 200 (4), 169 (100).

Anal. Calc. for C$_{13}$H$_{12}$N$_2$O$_3$: C 63.93, H 4.95, N 11.47; found: C 61.83, H 4.88, N 11.07.

EXAMPLE 3

N-{1-(1,2-Dihydronaphtho[2,1-b]furyl}-N-hydroxyurea 2-(2-Naphthoxy)acetic acid. To a solution of potassium hydroxide (10.0 g, 0.175 mol) in H$_2$O (100 mL) was added 2-naphthol (10.43 g, 72 mmol), followed by 2-chloroacetic acid (7.79 g, 83 mmol). The resulting mixture was heated at 70° C. for 4 h, then allowed to cool. The mixture was filtered, and the filtrate was extracted with EtOAc. The aqueous phase was made acidic by the addition of 3N HCl and extracted with EtOAc. The organic phase from the acidic extraction was washed successively with H$_2$O and saturated aqueous NaCl. The solvent was removed in vacuo to provide the title compound (2.11 g, 14%).

$^1$H NMR (CDCl$_3$/MeOH-d$_4$): $\delta$7.75 (m, 3H); 7.49–7.30 (m, 2H); 7.22 (dd, 1H); 7.11 (d, 1H); 4.70 (s, 2H); 4.52 (br s, 1H).

1,2-Dihydronaphtho[2,1-b]furan-1-one. A mixture of 2-(2-naphthoxy)acetic acid (3.06 g, 15.1 mmol) and oxalyl chloride (7 mL, 80.3 mmol) was heated at reflux for 45 min, then allowed to cool and concentrated under reduced pressure. The residue was dissolved in toluene, and to this was added aluminium chloride (2.40 g, 18.1 mmol). The resulting mixture was stirred at room temperature for 1 h, then poured into ice. The organic phase was separated and washed with saturated aqueous NaCl. Removal of the solvent in vacuo provided the title compound (2.71 g, 97%).

$^1$H NMR (CDCl$_3$/MeOH-d$_4$): $\delta$8.74 (d, 1H); 8.06 (d, 1H); 7.82 (d, 1H); 7.66 (ddd, 1H); 7.50 (ddd, 1H); 7.25 (d, 1H); 4.54 (s, 2H).

1,2-Dihydronaphtho[2,1-b]furan-1-one, oxime. To a solution of 1,2-dihydronaphtho[2,1-b]furan-1-one (2.71 g, 14.7 mmol) in pyridine (60 mL) was added hydroxylamine hydrochloride (2.00 g, 29.0 mmol). The resulting mixture was heated at 60° C. for 1.5 h, then allowed to cool to room temperature and concentrated under reduced pressure. The solid which formed was recrystallized from EtOH/H$_2$O to provide the title compound (1.87 g, 64%).

$^1$H NMR (CDCl$_3$/MeOH-d$_4$): $\delta$8.52 (br d, 1H); 7.84 (br d, 2H); 7.58 (apparent dt, 1H); 7.41 (apparent dt, 1H); 7.18 (d, 1H); 5.32 (s, 2H).

N-{1-(1,2-Dihydronaphtho[2,1-b]furyl}-N-hydroxyamine. To a solution of 1,2-dihydronaphtho[2,1-b]furan-1-one, oxime (1.73 g, 8.7 mmol) in EtOH (40 mL) was added BH$_3$.pyridine (35 g, 0.38 mol), and the resulting mixture was allowed to stir at room temperature. After stirring for 0.5 h, 3N HCl (175 mL) was added dropwise overnight. Ether was added to the reaction mixture, which was then cooled to 0° C. The pH was adjusted to basic by the addition of solid Na$_2$CO$_3$, and the organic phase was concentrated under reduced pressure. The residue was dissolved in EtOAc and washed successively with H$_2$O and saturated aqueous NaCl. The solvent was removed in vacuo to provide the title compound (0.61 g, 35%).

$^1$H NMR (CDCl$_3$/MeOH-d$_4$): $\delta$8.55–7.10 (m, 6H); 5.15 (dd, 1H); 4.90 (dd, 1H); 4.63 (dd, 1H).

N-{1-(1,2-Dihydronaphtho[2,1-b]furyl}-N-hydroxyurea. To a solution of N-{1-(1,2-dihydronaphtho[2,1-b]furyl}-N-hydroxyamine (698 mg, 3.5 mmol) in THF (10 mL) was added trimethylsilylisocyanate (0.94 mL, 7.0 mmol). The resulting solution was heated at 60° C. for 1 h, then allowed to cool and concentrated under reduced pressure. The residue was dissolved in EtOAc and washed successively with H$_2$O and saturated aqueous NaCl. The solvent was removed in vacuo. The residue was triturated with Et$_2$O and recrystallized from MeOH/CH$_2$Cl$_2$/hexanes to provide the title compound (93 mg, 11%). m.p. 194.5°–195.5° C.

$^1$H NMR (CDCl$_3$/MeOH-d$_4$): $\delta$7.86 (d, 1H); 7.80 (d, 1H); 7.78 (d, 1H); 7.48 (ddd, 1H); 7.31 (apparent dt, 1H); 7.11 (d, 1H); 6.48 (dd, 1H); 4.73 (m, 2H).

CIMS (NH$_3$); m/e (rel. int.): 262 (29), 246 (8), 184 (8), 169 (100), 94 (46).

Anal. Calc. for C$_{13}$H$_{12}$N$_2$O$_3$: C 63.93, H 4.95, N 11.47; found: C 62.85, H 5.09, N 11.34.

EXAMPLE 4

Capsule Composition

A pharmaceutical composition of this invention in the form of a capsule is prepared by filling a standard two-piece hard gelatin capsule with 50 mg. of a compound of Formula (I), in powdered form, 110 mg. of lactose, 32 mg. of talc and 8 mg. of magnesium stearate.

EXAMPLE 5

Ointment Composition

Compound of Formula (I) 1.0 g
White soft paraffin to 100.0 g

The compound of Formula (I) is dispersed in a small volume of the vehicle and this dispersion is gradually incorporated into the bulk to produce a smooth, homogeneous product which is filled into collapsible metal tubes.

EXAMPLE 6

Topical Cream Composition

Compound of Formula (I) 1.0 g
Carbowax 200 20.0 g
Lanolin Anhydrous 2.0 g
White Beeswax 2.5 g
Methyl hydroxybenzoate 0.1 g
Distilled Water to 100.0 g The carbowax, beeswax and lanolin are heated together at 60° C. and added to a solution of methyl hydroxybenzoate. Homogenization is achieved using high speed stirring and the temperature is allowed to fall to 50° C. The compound of Formula (I) is added and dispersed throughout, and the composition is allowed to cool with slow speed stirring.

EXAMPLE 7

Topical Lotion Composition

Compound of Formula (I) 1.0 g
Sorbitan Monolaurate 0.6 g
Polysorbate 20 0.6 g
Cetostearyl Alcohol 1.2 g
Glycerin 6.0 g
Methyl Hydroxybenzoate 0.2 g
Purified Water B.P. to 100.00 ml The methyl hydroxybenzoate and glycerin are dissolved in 70 ml of the water at 75° C. The sorbitan monolaurate, polysorbate 20 and cetostearyl alcohol are melted together at 75° C. and added to the aqueous solution. The resulting emulsion is homogenized, allowed to cool with continuous stirring and the compound of Formula (I) is added as a suspension in the remaining water. The whole suspension is stirred until homogenized.

EXAMPLE 8

Composition for Administration by Inhalation

For an aerosol container with a capacity of 15-20 ml: Mix 10 mg of a compound of Formula (I) with 0.1-0.2% of a lubricating agent, such as Span 85 or oleic acid, and disperse such mixture in a propellant (c.a.), such as freon, preferably a combination of freon 114 and freon 12, and put into an appropriate aerosol container adapted for either intranasal or oral inhalation administration.

UTILITY EXAMPLES

I. Methods

For the in vitro experiments, compounds were dissolved at appropriate concentrations in ethanol or dimethylsulfoxide (DMSO) having a final concentration of less than or equal to 1.0%, and then diluted to their respective concentrations using the buffers indicated in the text.

Animals

In experiments when mice were used they were CD1 mice obtained from Charles River Breeding Laboratories, and within a single experiment the mice were age-matched. Their weight range was from 25 to 42 g. The test groups generally contained 3-6 animals.

5-Lipoxygenase Activity

The 5-lipoxygenase (5-LO) was isolated from extracts of RBL-1 cells. The assay for assessing inhibition of the 5-LO activity was a continuous assay which monitored the consumption of oxygen ($O_2$). The cell extract (100 ug) was preincubated with the inhibitor or its vehicle in 25 mM BisTris buffer (pH 7.0) that contained 1 mM EDTA, 1 mM ATP, 150 mM NaCl and 5% ethylene glycol for 2 minutes at 20° C. (total volume 2.99 ml). Arachidonic acid (10 uM) and $CaCl_2$ (2 mM) were added to start the reaction, and the decrease in $O_2$ concentration followed with time using a Clark-type electrode and the Yellow Spring $O_2$ monitor (type 53) (Yellow Springs, Ohio). The optimum velocity was calculated from the progress curves. All compounds were dissolved in ethanol with the final concentration of ethanol being 1% in the assay.

Drug-induced effects on enzyme activities are described as the concentration of drug causing a 50% inhibition of oxygen consumption ($IC_{50}$).

Eicosanoid Production from Human Monocytes in Vitro

Human monocytes were prepared from leukosource packs supplied by the American Red Cross. The leukosource packs were fractionated by a two-step procedure described by F. Colatta et al. (*J. Immunology* 132: 936, 1984) that uses sedimentation on Ficoll followed by sedimentation on Percoll. The monocyte fraction that results from this technique was composed of 80-90% monocytes with the remainder being neutrophils and lymphocytes. In addition, significant number of platelets are present.

The monocytes ($10^6$ cells) were placed into polypropylene tubes and used as a suspended culture. The assay buffer consisted of RPMI 1640 buffer, 2 mM glutamine, 2.5 mM HEPES and 2 mM $CaCl_2$ (total volume 0.475 ml). Compounds (0.005 ml) were added in DMSO, and the cells were preincubated for 10 minutes at 37° C. with constant agitation. A23187 (2 uM) was used to stimulate the cells. After an additional 10 minutes, the buffer was collected by centrifugation (2500×g for 15 minutes), and stored at −70° C. until assayed. $LTB_4$ production was measured by radioimmunassay which was performed according to the manufacturer's (Advanced Magnetics, Boston, Mass.) instructions. $PGE_2$ was determined using an RIA kit supplied by New England Nuclear (Boston, Mass.).

Ex Vivo Mouse Blood Eicosanoid Assay

Mice were pre-treated per os with vehicle or a test compound (dissolved in dimethylacetamide and diluted 1 to 10 with sesame oil) 30 minutes prior to removal of blood. The 5-lipoxygenase product $LTB_4$, was extracted from whole blood following A23187 stimulation. Aliquots of pooled heparinized mouse blood (1 ml each aliquot) from male CD1 mice (Charles River) were placed into 4 ml polypropylene tubes. The tubes were preincubated for about five minutes at 37° C. A23187 (60 uM) was added to stimulate eicosanoid production. Several aliquots of blood were not stimulated and, thus, provided background levels for eicosanoid production. All tubes were incubated for about 30 minutes at 37° C. The blood samples were centrifuged at 400×g for about 15 minutes, and the plasma recovered for extraction. One volume of chilled acetonitrile was added to all at 5° C. The supernatants were recovered and diluted with 1% formic acid: 1% triethylamine to achieve a final concentration of 20% acetonitrile. These supernatants were then loaded onto the extraction cartridge that had been conditioned according to the Manufacturer's instructions (Solid Phase Extraction Columns, J. T. Baker, C18 3 ml size). The samples were washed with 3 ml of 1% formic acid: 1% triethylamine, air dried, and then washed with 3 ml of petroleum ether. After air drying again, the samples were eluted with methyl formate. The eluents were concentrated under vacuum. The concentrates were resuspended in 30% acetonitrile buffered with 50 mM ammonium acetate (200 ul). The recovery of $LTB_4$ was 60%. The 300 ul concentrates were assayed by radioreceptor assay for $LTB_4$ by labortatory protocol.

Inhibition of the Eicosanoid Production Following Calcium Ionophore (60 $\mu$M) Stimulation in Human Whole Blood The eicosanoids, which include the 5-lipoxygenase product $LTB_4$, trans$LTB_4$, 20-hydroxy$LTB_4$, 5-HETE, and the 12-lipoxygenase product are extracted from the whole blood following A23187 calcium ionophore stimulation. The extracts are separated by reverse phase high pressure liquid chromatography and quantified by absorbance methods.

Venous human blood is collected into polypropylene tubes containing 1% heparin. The blood is then aliquoted into 4.5 ml volumes and preincubated at 37° C. for 6 minutes in polypropylene tubes (15 ml size). Compound or carrier (10 $\mu$L dimethylsulfoxide) is added 6 minutes prior to stimulation. Calcium ionophore (0.5 ml) is added, and the blood incubated for 6 minutes. Prostaglandin $B_2$ (1 nmole) is added, and the blood extracted as described below.

The samples are centrifuged at 1000×g for 15 minutes at 5° C. The plasma is collected, and one volume of acetonitrile is added to the plasma. This suspension is then centrifuged at 1000×g for 15 minutes at 5° C. The supernatant is collected and diluted with 1.5 volumes of chilled aqueous 1% formic acid. This mixture is loaded onto a preconditioned J. T. Baker C18 SPE cartridge (Phillipsburg, N.J.) at a flow rate of 1-2 ml/minute. (The cartridge is preconditioned according to manufacture's recommendations.) The absorbed sample is washed in the following order with three (3) ml each of (i) aqueous 1% formic acid: 1% triethylamine; and (ii) petroleum ether.

The eicosanoids are eluted in 3 ml of methyl formate. The solvent is removed under vacuum. The sample is resuspended in 300 mL of 50% acetonitrile buffered with ammonium acetate.

The sample (200 ml) is loaded into a WATERS (Milford, Mass.) RCM NOVA PAK C18 (100×8 mm) column with the starting mobile phase of 90% A (A=10% acetonitrile buffered with 30 mM ammonium acetate to pH 5.8) and 10% B (B=90% acetonitrile buffered with 30 mM ammonium acetate to pH 6.8). The flow rate for the separation is 2.5 ml/minute. At one minute the % B is increased to 27% in a step fashion. By 12 minutes the % B has increased in a concave hyperbolic function (curve 9) to 40% and increases in a linear manner to 60% by 22 minutes.

Under these developing conditions, the retention times for the eicosanoids are: 20-hydroxyLTB$_4$, 4.6 minutes; thromboxane B$_2$, 6.5 minutes; transLTB$_4$, 10 minutes; LTB$_4$, 10.5 minutes; 12-HETE, 10.4 minutes; 5-HETE, 21 minutes. The HPLC system consisted of WATERS 510 pumps, 840 controller, WISP injector and 990 detector.

The eicosanoids in the samples are verified by their retention times and their UV absorbance spectra. The peaks are quantified with reference to the internal standard and their absorbance response at their maximum absorbance wavelength.

DATA ANALYSIS AND STATISTICS

Mean values for groups were calculated and percent inhibition was determined between the vehicle control mean and test group. The ED$_{50}$ was determined using linear regression analysis and was taken as the dose which resulted in a 50% inhibition of the vehicle control constriction response. Statistical analysis was done using Student's "t" test and a $p<0.05$ was considered statistically significant.

RESULTS

The hydroxyurea compounds of Examples 1-3, showed activity as inhibitors of the 5-LO enzyme having IC$_{50}$s in the RBL-1 supernatant 5-LO enzyme assay of 4.2-8.0 uM (Table 1). Examination of the activity of the compound of example 1, N-1-(1,2,3,4-Tetrahydrophenanthrenyl)-N-hydroxyurea, on the production of LTB$_4$ in the human monocyte corroborated the 5-LO inhibitory activity, IC$_{50}$ 1.6 uM. In contrast, the compound of example 1 did not inhibit cyclooxygenase activity as indicated by production of the prostaglandin PGE$_2$, IC$_{50}$ of greater than 30 uM.

Evaluation of the in vivo 5-LO inhibitory activity of these compounds was done using mouse whole blood stimulated with calcium ionophore (A23187) ex vivo. The compound of Example 1 inhibited 5-LO activity ex vivo by 86% at 10 mg/kg (ED$_{50}$=2.5 mg/kg).

TABLE 1

| example # | 5-LO IC-50, uM | ex vivo, % inh. @ 10 mg/kg | human monocyte-IC50, um LTB4 | PGE2 | human whole blood-IC50, uM |
|---|---|---|---|---|---|
| 1 | 4.2 | −86 | 1.6 | >30 | >10 |
| 2 | 5.6 | −92 | NT | NT | >10 |
| 3 | 8.0 | NT | NT | NT | >10 |

Discussion and Conclusion

The compounds of Formula (I) as shown herein by Example 1-3, inhibited 5-LO enzyme activity using isolated enzyme, whole cells and mouse blood, ex vivo. This inhibition of fatty acid oxygenase activity did not extend to cyclooxygenase and therefore, these are selective 5-LO inhibitors.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound of the formula

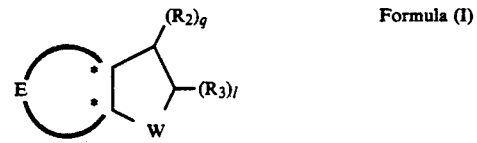

Formula (I)

wherein
R$_2$ and R$_3$ are

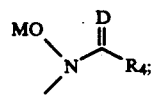

D is oxygen or sulfur;
M is hydrogen, a pharmaceutically acceptable cation, aroyl or —C(O)C$_{1-10}$ alkyl;
R$_4$ is NR$_5$R$_6$; alkyl$_{1-6}$; alkyl substituted by halogen or hydroxyl; alkenyl$_{2-6}$; aryl or heteroaryl optionally substituted by halogen, alkyl$_{1-6}$, halosubstituted alkyl$_{1-6}$, hydroxyl, or alkoxy$_{1-6}$;
R$_5$ is H or alkyl$_{1-6}$;
R$_6$ is H; alkyl$_{1-6}$; aryl; heteroaryl; arylalkyl; alkyl substituted by halogen or hydroxyl; aryl, heteroaryl, arylalkyl, or heteroarylalkyl substituted by halo, cyano, alkyl$_{1-12}$, alkoxy$_{1-6}$, halosubstituted alkyl$_{1-6}$, alkylthio, alkylsulphonyl, or alkylsulfinyl; or R$_5$ and R$_6$ may together form a ring having 5 to 7 members, which may optionally contain a heteroatom selected from oxygen, sulfur or nitrogen;

W is $CH_2(CH_2)_s$;

s is a number having a value of 0 to 2;

q is a number having a value of 0 or 1;

l is a number having a value of 0 or 1; provided that when q is 0 then l is 1, and $R_2$ is hydrogen and when q is 1 then l is 0 and $R_3$ is hydrogen;

E is selected from

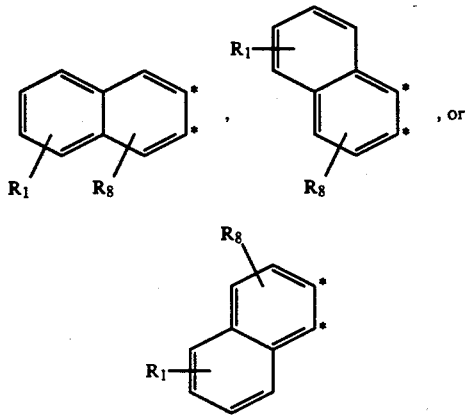

the asterisk * denoting point of attachment of the ring;

$R_1$ and $R_8$ are independently selected from the group consisting of hydrogen, halo, alkyl$_{1-10}$, halo-substituted $C_{1-10}$alkyl, hydroxy-substituted $C_{1-10}$ alkyl, alkoxy$_{1-10}$, —$(CH_2)_pCO_2R_5$, $(CH_2)_m$—Ar—$(X)_v$, $O(CH_2)_m$Ar—$(X)_v$, or $S(CH_2)_m$—Ar—$(X)_v$, provided that at least one of $R_1$ or $R_8$ is hydrogen, $C_{1-10}$ alkoxy, or halo;

m is a number having a value of 0 to 3;

p is a number having a value of 0 to 10;

v is a number having a value of 1 to 3;

Ar is a member selected from the group consisting of phenyl, naphthyl, quinolyl, isoquinolyl, pyridyl, furanyl, imidazoyl, benzimidazoyl, triazolyl, oxazolyl, isoxazolyl, thiazole, or thienyl;

X is a member selected from the group consisting of hydrogen, halogen, alkyl$_{1-5}$, cycloalkyl$_{5-8}$, hydroxy, (CHY)$_t$carboxy, O-alkyl$_{1-5}$, S(O)$_n$-alkyl$_{1-5}$, halosubstituted alkyl$_{1-5}$, (CHY)$_t$N(R$_5$)$_2$ or cyano; provided that if v is a number greater than 1 then one substituent must be selected from alkyl, O-alkyl$_{1-5}$, or halo;

Y is hydrogen or alkyl$_{1-3}$;

n is a number having a value of 0 to 2;

t is a number having a value of 0 or 1;

and the pharmaceutically acceptable salts thereof.

2. The compound according to claim 1 wherein W is $CH_2(CH_2)_s$, and s is a number having a value of 0 or 1.

3. The compound according to claim 2 wherein D is oxygen, and q is 1.

4. The compound according to claim 3 wherein $R_4$ is alkyl$_{1-6}$, halosubstituted alkyl$_{1-6}$, hydroxy substituted alkyl$_{1-6}$, alkenyl$_{2-6}$, aryl or heteroaryl optionally substituted by halogen, alkyl$_{1-6}$, halosubstituted alkyl$_{1-6}$, hydroxyl, or alkoxy$_{1-6}$.

5. The compound according to claim 3 wherein $R_4$ is $NR_5R_6$.

6. The compound according to claim 5 wherein $R_1$ is hydrogen, halo, $C_{1-10}$ alkoxy, $O(CH_2)_m$—Ar—$(X)_v$, $(CH_2)_m$—Ar—$(X)_v$, or $(CH_2)_pCO_2R_5$; m is a number having a value of 0 to 2; and v is a number having a value of 1 to 2.

7. The compound according to claim 6 wherein $R_5$ and $R_6$ are independently hydrogen or alkyl$_{1-6}$.

8. The compound according to claim 4 wherein $R_1$ is hydrogen, halo, $C_{1-10}$ alkoxy, halo substituted alkyl, $O(CH_2)_m$—Ar—$(X)_v$, $(CH_2)_m$—Ar—$(X)_v$, or $(CH_2)_pCO_2R_5$; m is a number having a value of 0 to 2; and v is a number having a value of 1 to 2.

9. The compound according to claim 5 wherein E is

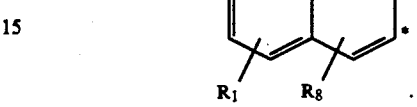

10. The compound according to claim 9 wherein $R_8$ is hydrogen, alkoxy, or halo.

11. The compound according to claim 5 wherein E is

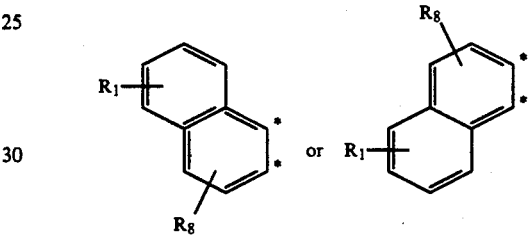

12. The compound according to claim 11 wherein $R_8$ is hydrogen, alkoxy, or halogen.

13. The compound according to claim 1 which is: N-1-(1,2,3,4-Tetrahydrophenanthrenyl)-N-hydroxyurea.

14. A pharmaceutical composition which comprises a pharmaceutically acceptable carrier or diluent and a compound of claim 1 or a pharmaceutically acceptable salt thereof.

15. The pharmaceutical composition according to claim 14 wherein the compound is N-1(1,2,3,4-Tetrahydrophenanthrenyl)-N-hydroxyurea.

16. The pharmaceutical composition according to claim 14 wherein $R_4$ is $NR_5R_6$.

17. The pharmaceutical composition according to claim 16 wherein $R_1$ is hydrogen, halo, $C_{1-10}$ alkoxy, $O(CH_2)_m$—Ar—$(X)_v$, $(CH_2)_m$—Ar—$(X)_v$, or $(CH_2)_pCO_2R_5$; m is a number having a value of 0 to 2; and v is a number having a value of 1 to 2.

18. A method of treating an oxygenated polyunsaturated fatty acid (OPUFA) mediated disease in a mammal in need thereof, which process comprises administering to such mammal an effective OPFUA inhibiting amount of a compound according to claim 1, or pharmaceutical salt thereof.

19. The method according to claim 18 wherein the enzyme 5-lipoxygenase is inhibited.

20. The method according to claim 19 wherein the lipoxygenase mediated disease is arthritis, rheumatoid arthritis, osteoarthritis, allergic rhinitis, psoriasis, dermatitis, ischemic induced myocardial injury, reperfusion injury, gout, asthma, adult respiratory distress syndrome, atherosclerosis, inflammatory bowel disease, stroke, spinal cord injury or traumatic brain injury.

* * * * *